US009375397B2

(12) United States Patent
Bettinger et al.

(10) Patent No.: US 9,375,397 B2
(45) Date of Patent: Jun. 28, 2016

(54) COMPOSITION COMPRISING GAS-FILLED MICROCAPSULES FOR ULTRASOUND MEDIATED DELIVERY

(75) Inventors: Thierry Bettinger, Peillonnex (FR); Feng Yan, Grand-Lancy (CH); Sophie Mehier-Humbert, Cruseilles (FR); Peter Frinking, Geneva (CH)

(73) Assignee: BRACCO SUISSE S.A., Manno (CH)

( * ) Notice: Subject to any disclaimer, the term of this patent is extended or adjusted under 35 U.S.C. 154(b) by 0 days.

(21) Appl. No.: 13/096,256

(22) Filed: Apr. 28, 2011

(65) Prior Publication Data

US 2011/0208115 A1 Aug. 25, 2011

Related U.S. Application Data

(62) Division of application No. 11/918,564, filed as application No. PCT/EP2006/061517 on Apr. 11, 2006, now abandoned.

(30) Foreign Application Priority Data

Apr. 18, 2005 (EP) .................................... 05103091

(51) Int. Cl.
*A61K 48/00* (2006.01)
*A61K 9/00* (2006.01)
*A61K 41/00* (2006.01)
*A61K 47/48* (2006.01)

(52) U.S. Cl.
CPC ........... *A61K 9/0009* (2013.01); *A61K 41/0028* (2013.01); *A61K 47/48869* (2013.01); *A61K 48/0008* (2013.01)

(58) Field of Classification Search
None
See application file for complete search history.

(56) References Cited

U.S. PATENT DOCUMENTS

| 4,276,885 A | 7/1981 | Tickner et al. |
| 4,543,101 A | 9/1985 | Crouch |
| 4,888,398 A | 12/1989 | Bichon et al. |
| 5,271,928 A | 12/1993 | Schneider et al. |
| 5,413,774 A | 5/1995 | Schneider et al. |
| 5,445,813 A | 8/1995 | Schneider et al. |
| 5,556,610 A | 9/1996 | Yan et al. |
| 5,585,112 A * | 12/1996 | Unger et al. .................. 424/450 |
| 5,597,549 A | 1/1997 | Schneider et al. |
| 5,711,933 A | 1/1998 | Bichon et al. |

(Continued)

FOREIGN PATENT DOCUMENTS

| EP | 0130935 B1 | 4/1987 |
| EP | 0240144 A1 | 7/1987 |

(Continued)

OTHER PUBLICATIONS

WG Pitt, GA Husseini, BJ Staples. "Ultrasonic Drug Delivery—A General Review." Expert Opinion in Drug Delivery, vol. 1(1), 2004, pp. 37-56.*

(Continued)

*Primary Examiner* — Isaac Shomer
(74) *Attorney, Agent, or Firm* — Vivicar Law, PLLC

(57) ABSTRACT

Composition comprising gas filled microcapsules and a bioactive agent, useful for an ultrasound-mediated delivery of said bioactive agent. The microcapsules comprise a relatively stiff shell of polymeric or lipid material and have in particular a resistance to a mechanical index of at least 0.15, while the bioactive agent is substantially unbound to the shell of the microcapsules. The composition of the invention is particularly suitable for effectively delivering a genetic material into a cell, upon exposure of the composition to a level of acoustic pressure capable of destroying a portion of the microcapsules and releasing the gas contained therein.

16 Claims, 3 Drawing Sheets

(56) References Cited

U.S. PATENT DOCUMENTS

| | | | |
|---|---|---|---|
| 5,827,504 | A | 10/1998 | Yan et al. |
| 5,830,430 | A | 11/1998 | Unger et al. |
| 5,837,221 | A | 11/1998 | Bernstein et al. |
| 6,045,777 | A | 4/2000 | Church et al. |
| 6,068,857 | A | 5/2000 | Weitschies et al. |
| 6,139,819 | A | 10/2000 | Unger et al. |
| 6,333,021 | B1 | 12/2001 | Schneider et al. |
| 6,416,740 | B1 | 7/2002 | Unger |
| 2002/0151792 | A1* | 10/2002 | Conston et al. ............... 600/439 |
| 2002/0159952 | A1* | 10/2002 | Unger .......................... 424/9.51 |
| 2003/0036697 | A1* | 2/2003 | Ottoboni .............. A61K 49/223 600/431 |
| 2003/0073903 | A1* | 4/2003 | Sato ...................... A61B 5/416 600/437 |
| 2003/0157025 | A1* | 8/2003 | Unger et al. ................. 424/9.52 |
| 2004/0258760 | A1 | 12/2004 | Wheatley et al. |

FOREIGN PATENT DOCUMENTS

| | | |
|---|---|---|
| EP | 0554213 A1 | 4/1993 |
| EP | 0324938 B1 | 11/1993 |
| EP | 0554213 B1 | 1/1997 |
| EP | 0554213 B2 | 8/2004 |
| GB | 486442 A | 6/1938 |
| JP | 60-141837 A | 7/1985 |
| JP | 62-253069 A | 11/1987 |
| JP | 5-255127 A | 10/1993 |
| JP | 11-503627 A | 3/1999 |
| JP | 2001-524983 A | 12/2001 |
| WO | 87/03891 A1 | 7/1987 |
| WO | 94/09829 A1 | 5/1994 |
| WO | 96/29113 A1 | 9/1996 |
| WO | 98/18501 A2 | 5/1998 |
| WO | 98/18501 A3 | 5/1998 |
| WO | 98-51284 A1 | 11/1998 |
| WO | 99/39697 A1 | 8/1999 |
| WO | 99/55383 A2 | 11/1999 |
| WO | 99/55383 A3 | 11/1999 |
| WO | 01/12069 A1 | 2/2001 |
| WO | 2004/069284 A3 | 8/2001 |
| WO | 02/05544 A1 | 1/2002 |
| WO | 02-055544 A2 | 7/2002 |
| WO | 03/074005 A2 | 9/2003 |
| WO | 03/084574 A1 | 10/2003 |
| WO | 2004/069284 A2 | 8/2004 |

OTHER PUBLICATIONS

Y Taniyama, K Tachibana, K Hiraoka, T Namba, K Yamasaki, N Hayisha, M Aoki, T Ogihara, K Yasufumi, R Morishita. "Local Delivery of Plasmid DNA Into Rat Carotid Artery Using Ultrasound." Circulation, vol. 105, 2002, pp. 1233-1239.*

C Sonne, F Xie, J Lof, J Oberdorfer, P PHillips, EC Everbach, TR Porter. "Differences in Definity and Optison Microbubble Destruction Rates at a Similar Mechanical Index with Different Real-time Perfusion Systems." Journal of the American Society of Echocardiography, vol. 16 No. 11, 2003, pp. 1178-1185.*

Y Taniyama, K Tachibana, K Hiraoka, T Namba, K Yamasaki, N Hashiya, M Aoki, T Ogihara, K Yasufumi, R Morishita. "Local Delivery of Plasmid Dna Into Rat Carotid Artery Using Ultrasound." Circulation, vol. 105, 2002, pp. 1233-1239.*

M-X Tang, H Mulvana, T Gauthier, AKP Lim, DO Cosgrove, RJ Eckersley, E Stride. "Quantitative contrast-enhanced ultrasound imaging: a review of sources of variability." Interface Focus, vol. 1, 2011, pp. 520-539.*

VP Torchilin. "Recent Approaches to Intracellular Delivery of Drugs and DNA and Organelle Targeting." Annual Reviews in Biomedical Engineering. vol. 8, 2006, pp. 343-375.*

PCT International Search Report for PCT/EP2006/061517, mail date Jul. 25, 2006.

PCT Written Opinion of the International Searching Authority for PCT/EP2006/061517, mail date Jul. 25, 2006.

PCT International Preliminary Report on Patentability for PCT/EP2006/061517, mail date Nov. 1, 2007.

Frinking, P.J.A. et al., "Effect of ultrasound on the release of microencapsulated drugs", Ultrasonics, IPC Science and Technology Press Ltd. Guilford, GB, vol. 36, No. 1-5, Feb. 1998, pp. 709-712, XP004119570, ISSN: 0041-624X.

Gorce, J-M et al., "Influence of Bubble Size Distribution on the Echogenicity of Ultrasound Contrast Agents, A Study of SonoVue TM", Investigative Radiology, vol. 35, No. 11, pp. 661-671, 2000, Lippincott Williams & Wilkins, Inc.

Huang, S-L et al., "Acoustically active liposomes for drug encapsulation and ultrasound-triggered release", Biochimica et Biophysica ACTA. Biomembranes, Amsterdam, NL, vol. 1665, No. 1-2, Oct. 11, 2004, pp. 134-141, XP004592242, ISSN: 0005-2736.

Miller, Douglas L. et al., "Sonoporation of Cultured Cells in the Rotating Tube Exposure System", Ultrasound in Medicine and Biology, 1999, vol. 25, No. 1, pp. 143-149, World Federation for Ultrasound in Medicine & Biology, Elsevier.

Sonne, Carolin et al., "Differences in Definity and Optison Microbubble Destruction Rates at a Smilar Mechanical Index with Different Real-tine Perfusion Systems", Journal of the American Society of Echocardiography, 2003, vol. 16, No. 11, pp. 1178-1185, doi:10.1067/j.echo.2003.07.001.

Office Action for European application No. 06725707.1, mail date Mar. 5, 2008.

Office Action for Japanese application No. 2008-507051, mail date Nov. 15, 2011 (English translation).

* cited by examiner

COMPOSITION COMPRISING GAS-FILLED MICROCAPSULES FOR ULTRASOUND MEDIATED DELIVERY

CROSS-REFERENCE TO RELATED APPLICATIONS

This application is a divisional of co-pending U.S. Ser. No. 11/918,564, filed Oct. 12, 2007, which is the national stage application of corresponding international application number PCT/EP2006/061517 filed Apr. 11, 2006, which claims priority to and the benefit of the European application no. 05103091.4. filed Apr. 18, 2005, all of which are hereby incorporated by reference in their entirety.

FIELD OF THE INVENTION

The present invention relates to the use of a composition comprising gas filled microcapsules and a bioactive agent for preparing a formulation for ultrasound-mediated delivery of a bioactive agent and to a method for delivery of a bioactive agent which comprises administering an effective amount of said medicament to a patient in need thereof.

BACKGROUND OF THE INVENTION

Ultrasound contrast agents (UCA) have been widely used in diagnostic applications in medical research and clinical practice. Typically, said UCA are in the form of stabilized gas-bubbles, also known as gas-filled microvesicles. Gas-filled microvesicles are in general divided into two main categories, i.e. microbubbles and microcapsules (or microballoons).

Microbubbles include aqueous suspensions in which the bubbles of gas are bounded at the gas/liquid interface by a thin envelope (film) involving a stabilizing amphiphilic material disposed at the gas to liquid interface. Microbubbles suspensions are typically prepared by contacting powdered amphiphilic materials, e.g. freeze-dried preformed liposomes or freeze-dried or spray-dried phospholipid solutions, with air or other gas and then with an aqueous carrier, while agitating to generate a microbubble suspension which can then be administered, preferably shortly after its preparation. Examples of aqueous suspension of gas microbubbles and preparation thereof are disclosed, for instance, in U.S. Pat. No. 5,271,928, U.S. Pat. No. 5,445,813, U.S. Pat. No. 5,413,774, U.S. Pat. No. 5,556,610, U.S. Pat. No. 5,597,549, U.S. Pat. No. 5,827,504 and WO 04/069284.

Microcapsules (or microballoons) include suspensions in which the bubbles of gas are surrounded by a solid material envelope of a lipid or of natural or synthetic polymers. The thickness of microcapsules envelope may vary from few nanometers to few hundreds of nanometers. Examples of microcapsules and of the preparation thereof are disclosed, for instance, in U.S. Pat. No. 5,711,933 and U.S. Pat. No. 6,333,021.

Recently, these UCA have been exploited in ultrasound-mediated gene delivery. This novel approach uses acoustic cavitation effects of gas microvesicles to induce transient membrane permeabilization at the cellular level (also known as "sonoporation"), thereby facilitating the transfer of drugs or genetic materials into the cell. Gas-filled microvesicles compositions have thus been developed, where the microvesicles contain, either in their internal void portion or embedded into the stabilizing envelope, a therapeutic compound. For instance, U.S. Pat. No. 6,416,740 discloses a targeted therapeutic system comprising gas-filled microspheres incorporating a therapeutic compound. Similarly, US Patent application no. 2004/0258760 relates to polymeric microcapsules loaded with a bioactive compound. This solution has however the disadvantage that the therapeutic compound has to be somehow inserted into the or attached to the gas-filled microvesicle, thus entailing cumbersome manufacturing processes. In addition, the fact that same microvesicle carrying the therapeutic compounds shall undergo to the cavitation effects to provide the necessary cellular permeabilization renders the whole system rather ineffective. Furthermore, as the therapeutic compound is in general hydrophobic or has to be rendered hydrophobic (e.g. in the case of genetic material) for it to be compatible with the material forming the microvesicles, the release of the therapeutic compound may be less effective in the hydrophilic environment of the blood circulation or of the cells.

The Applicant has now found that the use of a composition comprising gas-filled microcapsules having a predetermined resistance to the mechanical index of the applied ultrasound wave notably enhances the effectiveness of the delivery of therapeutic compounds (such as genetic material) into the cell, particularly when said therapeutic compound material is substantially free of any stable binding with the shell of said microcapsules.

SUMMARY OF THE INVENTION

An aspect of the present invention relates to a composition comprising a bioactive agent and gas-filled microcapsules having a polymeric and/or lipid shell, wherein said microcapsules have a resistance to a mechanical index (MI) of at least 0.15 and said bioactive agent is substantially unbound to said shell.

The term "resistance to MI" means that the microcapsules of a composition of the invention can withstand a predetermined threshold value of acoustic pressure applied at a predetermined frequency without suffering substantial damages. In particular, less than 50% of the total number of microcapsules, preferably less than 30% and even more preferably less than 20% of said microcapsules, is destroyed upon application of said predetermined threshold value of acoustic pressure. "Destruction" of microcapsules means that at least a portion of the shell of the microcapsule is destroyed, to release the gas contained therein.

The mechanical index (MI) as used herein is dimensionless, being defined as:

$$MI = \frac{P}{C_{MI}\sqrt{f}}$$

wherein P is the peak negative acoustic pressure (in MPa, measured in water), f the frequency (in MHz) of the applied ultrasound wave and $C_{MI}$ is a normalization constant which equals 1 MPa·MHz$^{1/2}$.

The term "substantially unbound" as used herein indicates that the bioactive agent has no stable interaction (e.g. of covalent or ionic type) with the molecules forming the envelope of the microcapsules and is thus freely dispersed in the suspension (outside the stabilizing envelope of the microvesicle). In particular, a composition according to the invention is an aqueous suspension comprising microcapsules and a bioactive agent (optionally associated with a carrier), the majority of said bioactive agent (i.e. more than 50%) being dissociated from the envelope of said microcapsules. Preferably, at least 75%, more preferably at least 90% of the total amount of said bioactive agent is freely dispersed (i.e. not stably bound to and not incorporated into the microcapsules) in said suspension.

Preferably, said microcapsules have a resistance to a mechanical index of at least 0.18 and more preferably of at least 0.20. In particular, said microcapsules have a resistance to an acoustic pressure of at least about 200 kPa at 1.15 MHz or of at least about 300 kPa at 2.25 MHz.

Preferably, the microcapsules of the composition have a stiffness of at least 5 N/m, more preferably of at least 8 N/m.

According to a preferred embodiment said bioactive agent is incorporated in a carrier. Preferably said carrier comprises a positively charged lipid or polymer. More preferably, said carrier is in the form of a micelle or of a liposome.

According to a further preferred embodiment said carrier further comprises a targeting ligand.

Another aspect of the invention relates to the use of a composition comprising a bioactive agent and gas-filled microcapsules having a polymeric and/or lipid shell for preparing a formulation for ultrasound-mediated delivery of said bioactive agent, wherein said microcapsules have a resistance to a mechanical index (MI) of at least 0.15 and said bioactive agent is substantially unbound to said shell.

A further aspect of the invention relates to a pharmaceutical kit comprising a bioactive agent and gas-filled microcapsules as above defined.

A still further aspect of the invention relates to a method for delivering a bioactive agent into a cell which comprises:
  administering a composition comprising a bioactive agent and a plurality of gas filled microcapsules having a polymeric and/or lipid shell to a body part comprising said cell in a patient in need thereof, said microcapsules having a resistance to a mechanical index of at least 0.15 and said bioactive agent being substantially unbound to said shell; and
  applying an ultrasound wave to said body part, said wave having an acoustic pressure capable of destroying a portion of said microcapsules, to effectively deliver said bioactive agent to said cell.

The portion of destroyed microcapsules can be also rather low, for instance 1% or less of the total number of microcapsules (e.g. when these are administered in high concentrations, e.g. $10^9$ microcapsules per ml of suspension). Preferably, the amount of destroyed microcapsules is of at least 5%, more preferably of at least 10% and even more preferably of at least 50%.

DRAWINGS

DETAILED DESCRIPTION

Figure 1A:
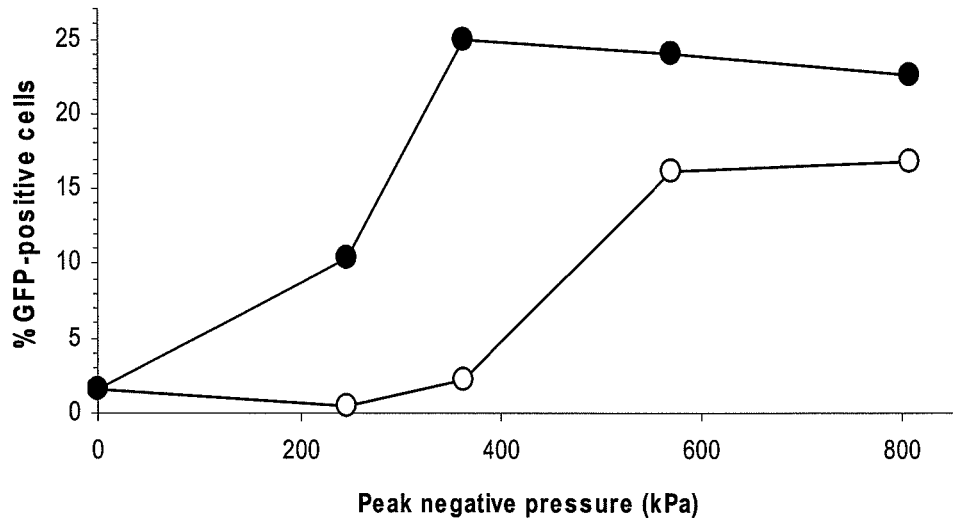
FIGS. 1a and 1b show the % of GFP-positive cells and the mean fluorescence intensities of positive cells measured upon ultrasound mediated gene delivery by using compositions containing microbubbles or microcapsules, at 2.25 MHz.

The pharmaceutically active composition of the invention can be used for effectively delivering a bioactive agent into a cell, by applying ultrasound waves, of predetermined acoustical pressure and frequency, capable of disrupting at least a portion of the microcapsules of the composition.

The term "pharmaceutically active composition" includes within its meaning any formulation, or precursor thereof, including bioactive and/or therapeutically active formulations, capable of exerting a pharmaceutical effect (e.g. a bioactive and/or therapeutic effect) when administered in an effective amount to a patient in need thereof. Similarly, the term "pharmaceutical active" when referred to a compound, an agent or kit includes within its meaning diagnostic, bioactive and/or therapeutic compounds, agents or kits.

The term "bioactive agent" includes within its meaning any substance, composition or particle capable of being used in a treatment (including diagnosis, prevention, alleviation, pain relief or cure) of any pathological status in a patient (including malady, affliction, disease lesion or injury), including compounds of formulations which may be used in any therapeutic application, such as in methods for the treatment of a disease in a patient, as well as any substance which is capable of exerting or responsible to exert a biological effect in vitro and/or in vivo. Examples of bioactive agents are drugs, pharmaceuticals, proteins, natural or synthetic peptides, including oligopeptides and polypeptides, vitamins, steroids and genetic material, including nucleosides, nucleotides and polynucleotides. A therapeutic method or treatment of a patient typically includes the use of a bioactive agent, typically included into a pharmaceutically active composition.

As observed by the Applicant, the use of microcapsules with a solid envelope made of a polymeric and/or lipid material (particularly those with an envelope thickness of at least 50 nm, preferably of at least 100 nm) allows a more effective delivery of genetic material into the cell, as compared to the use of microbubbles stabilized by thin films (e.g. less than 10 nm) of material.

The envelope of gas-filled microcapsules of a composition of the invention is preferably a polymeric envelope, preferably comprising a biodegradable polymer, or an envelope comprising biodegradable water-insoluble lipids. Examples of suitable microcapsules and of the preparation thereof are disclosed, for instance, U.S. Pat. No. 5,711,933, U.S. Pat. No. 6,333,021, U.S. Pat. No. 5,837,221 or U.S. Pat. No. 6,045,777, herein all incorporated by reference in their entirety. Microcapsules having a proteinaceous envelope, i.e. made of natural proteins (albumin, haemoglobin) such as those described in U.S. Pat. No. 4,276,885 or EP-A-0 324 938, can also be employed.

Polymers forming the envelope of the injectable microcapsules are preferably hydrophilic, biodegradable physiologically compatible polymers. Examples of such polymers, which may be natural or synthetic, are substantially insoluble polysaccharides (e.g. chitosan or chitin), polycyanoacrylates, polylactides and polyglycolides and their copolymers, copolymers of lactides and lactones such as γ-caprolactone or δ-valerolactone, copolymers of ethyleneoxide and lactides, polyethyleneimines, polypeptides, and proteins such as gelatin, collagen, globulins or albumins. Other suitable polymers mentioned in the above cited U.S. Pat. No. 5,711,933 include poly-(ortho)esters, polylactic and polyglycolic acid and their copolymers (e.g. DEXON®, Davis & Geck, Montreal, Canada); poly(DL-lactide-co-γ-caprolactone), poly(DL-lactide-co-δ-valerolactone), poly(DL-lactide-co-γ-butyrolactone), polyalkylcyanoacrylates; polyamides, polyhydroxybutyrate; polydioxanone; poly-β-aminoketones; polyphosphazenes; and polyanhydrides. Polyamino-acids such as polyglutamic and polyaspartic acids can also be used, as well as their derivatives, such as partial esters with lower alcohols or glycols. Copolymers with other amino acids such as methionine, leucine, valine, proline, glycine, alanine, etc. can also be used. Derivatives of polyglutamic and polyaspartic acid with controlled biodegradability (such as those described in WO87/03891, U.S. Pat. No. 4,888,398 or EP 130935, all herein incorporated by reference) can also be used. These polymers (and copolymers with other aminoacids) have formulae of the following type: —(NH—CHA-CO)$_w$—(NH—CHX—CO)$_y$— where X designates the side chain of an amino acid residue (e.g. methyl, isopropyl, isobutyl, or benzyl); A is a group of formula —(CH$_2$)$_n$COOR$^1$R$^2$—OCOR, —(CH$_2$)$_n$COO—CHR$^1$COOR, —(CH$_2$)$_n$CO(NH—CHX—CO)$_m$NH—CH(COOH)—(CH$_2$)$_p$COOH, or the respective anhydrides thereof, wherein R$^1$ and R$^2$ represent H or lower alkyls, and R represents alkyl or aryl; or R and R$^1$ are connected together by a substituted or unsubstituted linking member to provide 5- or 6-membered rings; n, m and p are lower integers, not exceeding 5; and w and y are integers selected for having molecular weights not below 5000.

Non-biodegradable polymers can also be used (e.g. for making microcapsules to be used in the digestive tract), optionally in combination with the above biodegradable polymers. These can be selected from most water-insoluble, physiologically acceptable, bioresistant polymers including, for example, polyolefins (polystyrene), acrylic resins (polyacrylates, polyacrylonitrile), polyesters (polycarbonate), polyurethanes, polyurea and their copolymers. ABS (acryl-butadiene-styrene) is a preferred copolymer.

Advantageously, ionic polymers (i.e. polymers bearing ionic moieties in their structure), preferably biodegradable ionic polymers, can also be used to form the stabilizing envelope of the microcapsules, thus conferring an overall net charge thereto. Ionic polymers can be used as main components of the stabilizing envelope or they can be admixed in various amounts (e.g. from 2 to 80% by weight) with non ionic polymers. Suitable ionic polymers are, for instance, polymers comprising a quaternized nitrogen atom, such as quaternized amines or polymers comprising carboxylic, sulphate, sulphonate or phosphonate moieties. Examples of suitable ionic polymers include, without limitation, poly(diallyldimethylammonium chloride), poly{bis(2-chloroethyl) ether-alt-1,3-bis[3-(dimethylamino)propyl]urea} quaternized (Polyquaternium®-2), poly(4-vinylpyridinium tribromide), hydroxyethylcellulose ethoxylate quaternized (Polyquaternium®-4, poly(p-xylene tetrahydrothiophenium chloride), poly(L-lysine), chitin, diethyleneaminoethyl dextran, poly(acrylic acid), poly(methacrylic acid), poly(styrene-alt-maleic acid), poly(amino acids), alginic acid, poly (uridylic acid), hyaluronic acid, i.e. poly(β-glucuronic acid-alt-β-N-acetylclucosamide), poly(galacturonic acid), poly (vinyl acetate-co-crotonic acid), poly(3,3',4,4'-benzophenonetetracarboxylic dianhydride-co-4,4'-oxydianiline), poly(isoprene-graft-maleic acid monomethyl ether), copolymer of glutamic acid with alkyl glutamate, heparin, poly(styrene sulphonate), sulfonated poly(isophthalic acid), poly(vinyl sulphonate, potassium salt), poly(vinyl sulphate, potassium salt), chondroitin sulfate A, dextran sulfate, fucoidan, polyphosphoric acid, sodium polyphosphate, sodium polyvinylphosphonate, chitosan, chitosan sulfate, sodium alginate, alginic acid and ligninsulfonate.

Biodegradable water-insoluble lipids useful for forming microcapsules for a composition according to the invention comprise, for instance, solid water insoluble mono-, di- or tri-glycerides, fatty acids, fatty acid esters, sterols such as cholesterol, waxes and mixtures thereof. Mono-, di- and tri-glycerides include mainly the mono-, di- and tri-laurin compounds as well as the corresponding -myristin, -palmitin, -stearin, -arachidin and -behenin derivatives. Mono-, di- and tri-myristin, -palmitin -stearin and mixed triglycerides such as dipalmitoylmonooleyl glyceride are particularly useful; tripalmitin and tristearin are preferred. Fatty acids include solid (at room temperature, about 18-25° C.) fatty acids (preferably saturated) having 12 carbon atoms or more, including, for instance, lauric, arachidic, behenic, palmitic, stearic, sebacic, myristic, cerotinic, melissic and erucic acids and the fatty acid esters thereof. Preferably, the fatty acids and their esters are used in admixture with other glycerides.

The sterols are preferably used in admixture with the other glycerides and or fatty acids and are selected from cholesterol, phytosterol, lanosterol, ergosterol, etc. and esters of the sterols with the above mentioned fatty acids; however, cholesterol is preferred.

Preferred biodegradable lipids are triglycerides such as tripalmitin, tristearin or mixtures of the above mentioned triglycerides.

Optionally, up to 75% by weight of a biodegradable polymer, such as those listed previously, can be admixed together with the biodegradable water insoluble lipid forming the envelope of the microcapsule.

Conventional additives can also be incorporated into the envelope of the microcapsules, to modify physical properties thereof, such as dispersibility, elasticity and water permeability. In particular, effective amounts of amphiphilic materials, such as lipids, phospholipids or modified phospholipids can be added to the emulsion prepared for the manufacturing of said microcapsules, in order to increase the stability thereof.

Other excipients or additives, in particular used for the preparation of microcapsules, can be incorporated into the envelope such as redispersing agents or viscosity enhancers.

Biodegradable polymer containing microcapsules can be prepared, for instance, according to the process disclosed in U.S. Pat. No. 5,711,933, herein incorporated by reference, which comprises (a) emulsifying a hydrophobic organic phase into a water phase so as to obtain droplets of said hydrophobic phase as an oil-in-water emulsion in said water phase; (b) adding to said emulsion a solution of at least one polymer in a volatile solvent insoluble in the water phase, so that said polymer forms a layer around said droplets; (c) evaporating said volatile solvent so that the polymer deposits by interfacial precipitation around the droplets which then form beads with a core of said hydrophobic phase encapsulated by a membrane of said polymer, said beads being in suspension in said water phase; (d) removing said encapsulated hydrophobic phase by evaporation by subjecting said suspension to reduced pressure; and (e) replacing said evaporated hydrophobic phase with a suitable gas.

Biodegradable lipid containing microcapsules can be prepared, for instance, according to the process disclosed in U.S. Pat. No. 6,333,021 (herein incorporated by reference), by dispersing a mixture of one or more of the solid constituents of the microcapsule envelope dissolved in an organic solvent in a water carrier phase, so as to produce an oil-in-water emulsion. The emulsion water phase may contain an effective amount of amphiphilic materials which are used to stabilise the emulsion.

A certain amount of redispersing agent and/or of a cryoprotecting or lyoprotecting agent, is then added to the emulsion of tiny droplets of the organic solution in the water phase, prior to freezing at a temperature below −30° C. Any convenient redispersing agent may be used; redispersing agents selected from sugars, albumin, gelatine, polyvinyl pyrolidone (PVP), polyvinyl alcohol (PVA), polyethylene glycol (PEG) and ethyleneoxide-propyleneoxide block copolymer (e.g. Pluronic®, or Synperonic®) or mixtures thereof are preferred. The redispersing agents which are added to prevent particle agglomeration are particularly useful when the microcapsules are in the form of non-coalescent, dry and instantly dispersible powders. Examples of cryoprotecting or lyoprotecting agent are for instance amino-acids such as glycine; carbohydrates, e.g. a sugar such as sucrose, mannitol, maltose, trehalose, glucose, lactose or a cyclodextrin, or polysaccharides such as dextran; or polyglycols such as polyethylene glycol.

The frozen emulsion is then subjected to reduced pressure to effect lyophilization, i.e. the removal by sublimation of the organic solvent from the droplets and of the water of the carrier phase, and the freeze-dried product is then contacted with the desired gas.

The microcapsules suitable for a composition of the invention typically have an envelope with a thickness of at least 50 nm, preferably of at least 100 nm, up to few hundred nanometers (e.g. about 600 nm). As observed by the applicant, the thickness of the envelope is one parameter which can be modulated to confer to said microcapsule the desired resistance to high values of MI.

It has further been observed that the desired properties of the microcapsules can also be modulated by suitably selecting the material forming the envelope, based on the knowledge of those skilled in the art in view of the present disclosure. For instance, when the material forming the envelope is a polymer, the desired properties can be obtained by selecting a suitable molecular weight of said polymer; typically said molecular weight shall preferably be of at least 30 kDa (kilo-Daltons), more preferably of at least 100 KDa and even more preferably of at least 300 kDa. Alternatively, or in addition thereto, the resistance to a predetermined MI can be increased by cross linking the molecules of the material forming the envelope (e.g. a lipid or a low molecular weight polymer) and/or by suitably increasing the thickness of the envelope.

In general, it may be advantageous to use materials for the envelope, capable to conferring a certain stiffness to the microcapsules.

The stiffness provided by the envelope, $S_p$, can be determined by a best fit analysis between measured and calculated attenuation spectra of the microvesicles (microbubbles or microcapsules). Attenuation is the result of energy dissipation due to absorption and scattering during propagation of the ultrasound wave through a volume filled with a suspension of microvesicles. Attenuation spectra are commonly measured using the substitution technique as described, for instance, by Gorce J M, Arditi, M and Schneider M. "Influence of bubbles size distribution of the echogenicity of ultrasound contrast agents: A study of SonoVue". Invest. Radiol., vol 35(11), pp. 661-671, 2000. Briefly, the acoustic response of a plane reflector, e.g. the back wall of a container filled with 0.9% NaCl, is measured and used as reference echo, $I_{ref}(\omega)$. Next, the 0.9% NaCl in the container is replaced by a suspension with the microvesicles, and the response of the back wall is measured again, $I_{atten}(\omega)$. The ratio of the two measurements results in the experimentally determined attenuation as a function of frequency:

$$\alpha_{exp}(\omega) = \frac{I_{atten}(\omega)}{I_{ref}(\omega)}.$$

Attenuation spectra can be calculated using theoretical models which are well known and extensively described in the literature (e.g. in the above cited reference of Gorce et al.). Briefly, based on a size distribution measurement of the microvesicles, e.g. with a Coulter Multisizer II (Coulter Electronics Ltd., Luton, UK), the attenuation spectrum is calculated for an initial value of $S_p$. An error criterion for the best-fit analysis is then computed as the root-mean-square (RMS) error between experimental and theoretical attenuation spectra. This attenuation error can be written as:

$$\Delta \alpha_{RMS} = \sqrt{\frac{\sum_{\omega_i} |\alpha_{exp}(\omega_i) - \alpha_{th}(\omega_i)|^2}{N}},$$

where $\omega_i = [\omega_1, \ldots, \omega_N]$ are the sampled frequencies used for the fit, and $\alpha_{th}(\omega)$ is the calculated attenuation as a function of frequency. The $S_p$ producing a minimal RMS error for the given size distribution is considered as best estimate.

According to the present invention, preferred microcapsules are those having a value of $S_p$ of at least about 5 N/m, preferably of at least about 8 N/m.

For the attenuation measurements, the following setup can be used. Two single element transducers, 7.5 MHz and 20 MHz (V3640 and V316, Panametrics Inc., Waltham, Mass.) are driven by an ultrasonic pulser-receiver (5800PR, Panametrics Inc., Waltham, Mass.) in pulse-echo (transmit and receive) mode. This way, a frequency band ranging from 5 to 25 MHz is covered. The output of the pulser-receiver is connected to a 50Ω input of a digital oscilloscope (DL4100 model, 10 bit, 100 MS/s, Yokogawa Electric Corp, Tokyo, japan). The pulser-receiver and the oscilloscope are controlled through a GPIB connection by a Personal Computer (PC). In this way, all steps of the acquisition are controlled by software (developed in-house using Delphi 4, Inprise Corp, Scotts Valley, Calif.). The Fourier spectra of the acquired signals, averaging and attenuation spectrum calculations are also performed by this software. The results and all acquisition parameters are saved on the PC. All modeling calculations and the best-fit analysis are performed with MATLAB© software (v7.04, The Math Works Inc., Natick, Mass.).

Whichever the material forming the rigid-shell envelope, the Applicant has observed that, in order to provide an effective penetration of the genetic material into the cell, the microcapsules of a composition according to the invention shall have a resistance to mechanical index of at least 0.15, preferably of at least 0.18 and even more preferably of at least 0.20. Preferably, the microcapsules do not resist at mechanical indexes higher than about 10, in order to avoid the need of applying acoustic pressures which may cause an excessively negative effect on the viability of the cells submitted to said ultrasound waves.

Any biocompatible gas, gas precursor or mixture thereof may be employed to fill the microcapsules of a composition of the invention.

The gas may comprise, for example, air; nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases. Fluorinated gases include materials which contain at least one fluorine atom such as, for instance fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable microbubble suspensions, as disclosed, for instance, in EP 0554 213, which is herein incorporated by reference.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoroisobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons have the formula $C_nF_{2n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_6F_{14}$, $C_7F_{14}$, $C_7F_{16}$, $C_8F_{18}$, and $C_9F_{20}$.

Particularly preferred gases are $SF_6$ or perfluorocarbons selected from $CF_4$, $C_2F_6$, $C_3F_8$, $C_4F_8$, $C_4F_{10}$ or mixtures thereof; $SF_6$, $C_3F_8$ or $C_4F_{10}$ are particularly preferred.

It may also be advantageous to use a mixture of any of the above gases in any ratio. For instance, the mixture may comprise a conventional gas, such as nitrogen, air or carbon dioxide and a fluorinated gas, such as sulfur hexafluoride or a perfluorocarbon as indicated above. Examples of suitable gas mixtures can be found, for instance, in WO 94/09829, which is herein incorporated by reference. The following combinations are particularly preferred: a mixture of gases (A) and (B) in which the gas (B) is a fluorinated gas, preferably selected from $SF_6$, $CF_4$, $C_2F_6$, $C_3F_6$, $C_3F_8$, $C_4F_6$, $C_4F_8$, $C_4F_{10}$, $C_5F_{10}$, $C_5F_{12}$ or mixtures thereof, and (A) is selected from air, oxygen, nitrogen, carbon dioxide or mixtures thereof. The amount of gas (B) can represent from about 0.5% to about 95% v/v of the total mixture, preferably from about 5% to 80%.

In certain circumstances it may be desirable to include a precursor to a gaseous substance (i.e. a material that is capable of being converted to a gas in vivo). Preferably the gaseous precursor and the gas derived therefrom are physiologically acceptable. The gaseous precursor may be pH-activated, photo-activated, temperature activated, etc. For example, certain perfluorocarbons may be used as temperature activated gaseous precursors. These perfluorocarbons, such as perfluoropentane or perfluorohexane, have a liquid/gas phase transition temperature above room temperature (or the temperature at which the agents are produced and/or stored) but below body temperature; thus, they undergo a liquid/gas phase transition and are converted to a gas within the human body.

The formulation of the invention further comprises a bioactive agent as above defined.

According to a preferred embodiment, the bioactive agent comprised in a composition of the invention is a genetic material. The term genetic material includes within its meaning any nucleic acid (or nucleotide sequence) which can be used either as such or for expressing a corresponding amino acid, peptide or protein once delivered into a cell. The genetic material delivered according to the method of the invention includes in particular nucleic acids, RNA, and DNA, of either natural or synthetic origin including recombinant RNA and DNA, antisense or antigen RNA. The term refers both to the nucleotide sequence (gene) as such or preferably to the gene incorporated into a suitable vehicle. Suitable vehicles for carrying the genes include expression vectors such as plasmids, phagemids, cosmids, yeast artificial chromosomes (YAC), bacterial artificial chromosomes (BAC), human artificial chromosomes (HAC), chimeric oligonucleotide comprising RNA and DNA residues in a duplex conformation, hairpin or hammerhead ribozyme, small interfering RNA (siRNA), siRNA expression cassettes, DNA ribonucleases, transposon, both single and double strand RNA and DNA and analog thereof, such as phosphorothioate, phosphorodithioate oligodesoxynucleotide.

Said genetic material can be used, for instance, for replacing missing or defective genes, for catalysing the destruction of cancer cells or causing cancer cells to revert back to normal tissue, for enhancing or stimulating an immune response, for promoting the growth of new tissue or stimulating regeneration of damaged tissue, for enabling repair of mutated or damaged genes, for catalysing endoribonucleolytic cleavage, for blocking gene expression by triplex formation or for blocking mRNA translation.

Examples of genetic material which may be delivered using the microcapsules of the present invention include DNA encoding for at least a portion of the following genes: cystic fibrosis transmembrane conductance regulator to treat cystic fibrosis (CFTR, regulates intracellular chloride), dystrophin to treat muscular dystrophy, adenosine deaminase to treat severe immunodeficiency, HDL receptor for the treatment of hypercholesterolemia, ApoE for the treatment of atherosclerosis, Factor VIII (Hemophilia A, Regulates blood coagulation), Factor IX (Hemophilia B, Regulates blood coagulation), gene expressing cytokines such as Interleukin-2 or Interleukin-4 or Interleukin-7, or Interleukin-12, or tumor necrosis factor α (TNF α) or tumor-infiltrating lymphocytes (TIL), or HLA-B7, for stimulating immune system to kill cancer cells or p53 tumor suppressor or herpes simplex virus thymidine kinase (HSV-TK) may be provided to treat cancer by causing cancer cells to undergo cell death, the vascular endothelial growth factor (VEGF) or the hepatocyte growth factor (HGF) or the fibroblast growth factor (FGF) may be provided to treat cardiovascular diseases by promoting angiogenesis, and alpha-melanocyte-stimulating hormone (alpha-MSH) may be provided to treat inflammation, melanin concentrating hormone for anti-obesity therapy, and HIV env or RNA interference may be provided to treat HIV infection. The wording "at least a portion of", as used herein, means that the entire gene need not to be represented by the oligonucleotide, so long as the portion of the gene represented provides an effective block to gene expression. If desired, more than one genetic material may be delivered using the microcapsules. Moreover, for some applications, nucleic acid may be conjugated to nuclear localization signal (NLS) to enhance nuclear delivery of plasmid DNA.

Genetic material may be used either as such in a composition of the invention or it can be associated with a suitable viral or non-viral carriers (e.g. to limit or avoid nuclease degradation of nucleic acid in the blood stream). The viral carriers comprise retroviruses, lentivirus, adenoviruses, adeno-associated virus, herpes virus, vaccinia virus, equine infectious anemia virus (EIAV), Sindbis and Semliki Forest alphavirus, Ebstein Barr Virus (EBV). This also comprises viruses with altered tropism, obtained by genetic modification of the capsid protein or chemical modification of the capsid surface with hydrophilic polymers and targeting ligand.

Non-viral carriers can be selected among known cationic lipids (i.e. lipids bearing an overall net positive charge) or polymers, which can associate with the negatively charged nucleotide sequences.

Examples of suitable cationic lipids which may be used (to form so-called lipoplexes) are, for instance, derivatives of ethylphosphatidylcholine, in particular esters of ethylphosphatidylcholine with fatty acids, such as 1,2-Distearoyl-sn-glycero-3-Ethylphosphocholine (Ethyl-DSPC or DSEPC), 1,2-Dipalmitoyl-sn-glycero-3-Ethylphosphocholine (Ethyl-DPPC or DPEPC). Examples of positively charged lipids are alkylammonium salts with a halogen counter ion (e.g. chlorine or bromine) comprising at least one ($C_{10}$-$C_{20}$), preferably ($C_{14}$-$C_{18}$), alkyl chain, such as, for instance stearylammonium chloride, hexadecylammonium chloride, dimethyldioctadecylammonium bromide (DDAB), hexadecyltrimethylammonium bromide (CTAB). Further examples of positively charged lipids are tertiary or quaternary ammonium salts with a halogen counter ion (e.g. chlorine or bromine) comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-dioleoyl-3-trimethylammonium-propane (DOTAP), 1,2-distearoyl-3-dimethylammonium-propane (DSDAP).

Synthetic cationic lipids can also be used, such as those disclosed in U.S. Pat. No. 5,830,430, herein incorporated by reference in its entirety. These include, for example, N,N'-bis (dodecyaminocarbonylmethylene)-N,N'-bis(β-N,N,N-trimethylammoniumethyl-aminocarbonylmethyleneethyl-enediamine tetraiodide; N,N''-bis hexadecylaminocarbonylmethylene)-N,N',N''-tris(β-N,N,N-trimethyl-ammonium-ethylaminocarbonylmethylene-diethylenetriamine hexaiodide; N,N'-Bis(dodecylaminocarbonylmethylene)-N,N''-bis(β-N,N,N-trimethylammonium-ethylaminocarbonylmethylene)cyclohexylene-1,4-diamine tetraiodide; 1,1,7,7-tetra-(β3-N,N,N,N-tetramethylammoniumethylaminocarbonylmethylene)-3-hexadecylaminocarbonyl-methylene-1,3,7-triaazaheptane heptaiodide; and N,N,N'N'-tetra phosphoethanolaminocarbonylmethylene) diethylenetriamine tetraiodide, dioctadecylamidoglycyl spermine (DOGS); 2-3-dioleyloxy-N-(2(sperminecarboxamido)ethyl)-N,N-dimethyl-1-propanaminium trifluoroacetate (DOSPA); dipalmitoyl phosphatidyl-ethanolamidospermine (DPPES); glycine betaine derivatives such as GB12; cationic lipids bearing unsaturated double chain based on 3,4-dihydroxybenzoic acid (MVL5); guanidine-containing lipids such as bis-guanidinium-tren-cholesterol (BGTC), cholesterol derivatives such as cholesteryl-3βcarboxyamidoethylene dimethyl amine (DC-Chol).

Optionally, the nucleic acid can also be pre-condensed with protamine sulphate (to form so-called "LDP-particles")

The above cationic lipids may also be formulated in combination with neutral and/or negatively charged lipids including, but not limited to phosphatidylcholines, such as dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC) or dioleoyl-phosphatidylcholine (DOPC); phosphatidylethanolamines such as dimyristoyl-phosphatidylethanolamine (DMPE), dipalmitoylphosphatidyl-ethanolamine (DPPE), distearoyl phosphatidyl-ethanolamine (DSPE), dioleylphosphatidyl-ethanolamine (DOPE), diarachidoylphosphatidyl-ethanolamine (DAPE) or dilinoleylphosphatidylethanolamine (DLPE); phosphatidylserines, such as dimyristoylphosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS); phosphatidic acid derivatives, such as dipalmitoyl phosphatidic acid (DPPA), dimyristoyl phosphatidic acid (DMPA), distearoyl phosphatidic acid (DSPA), diarachidoylphosphatidic acid (DAPA) and their alkali metal salts; phosphatidylglycerols such as dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG); phosphatidylinositols, such as dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI); PEG-modified phosphatidylethanolamines, such as DMPE-PEG1000, DMPE-PEG2000, DMPE-PEG3000, DMPE-PEG4000, DMPE-PEG5000, DPPE-PEG1000, DPPE-PEG2000, DPPE-PEG3000, DPPE-PEG4000, DPPE-PEG5000, DSPE-PEG1000, DSPE-PEG2000, DSPE-PEG3000, DSPE-PEG4000, DSPE-PEG5000, DAPE-PEG1000, DAPE-PEG2000, DAPE-PEG3000, DAPE-PEG4000 or DAPE-PEG5000; bile acid salts such as cholic acid salts, deoxycholic acid salts or glycocholic acid salts; and ($C_{12}$-$C_{24}$), preferably ($C_{14}$-$C_{22}$) fatty acid salts such as, for instance, palmitic acid salt, stearic acid salt, 1,2-dipalmitoyl-sn-3-succinylglycerol salt or 1,3-dipalmitoyl-2-succinylglycerol salt; cholesterol, or polymerized lipids (such as lipids comprising for example cysteine/or thiol moieties to enable oxidative polycondensation of lipids).

In addition also the fluorinated derivatives of the above lipids can advantageously be employed.

The obtained carrier containing the nucleic acid can be either in the form of a single complex of genetic material with the lipid (lipoplex) or a plurality of complexes can be associated together to form "supramolecular" structures such as, for instance, micelles or liposomes.

Alternatively or in addition to the above lipid formulations, nucleic acids can also be associated with polymers (to form so-called polyplexes or polymeric nanoparticles). Examples of suitable polymers are synthetic polymers or copolymers which are prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, cyanomethacrylate, bisphenol A, epichlorhydrin, hydroxyalkylacrylates, siloxane, dimethylsiloxane, ethylene oxide, ethylene glycol, hydroxyalkylmethacrylates, N-substituted acrylamides, N-substituted methacrylamides, N-vinyl-2-pyrrolidone, 2,4- pentadiene-1-ol, vinyl acetate, acrylonitrile, styrene, p-amino-styrene, p-aminobenzylstyrene, sodium styrene sulfonate, sodium 2-sulfoxyethyl-methacrylate, vinyl pyridine, aminoethyl methacrylates, lactides, and 2-methacryloyloxytrimethyl-ammonium chloride. Examples of synthetic (co-) polymers are, for instance, polyacrylic acid, polyethyleneimine, polymethacrylic acid, polymethylmethacrylate, polycyanomethacrylate, polyamidoamine dendrimers, organophosphorus dendrimers, polysiloxane, polydimethylsiloxane, polylactic acid, poly(ε-caprolactone), epoxy resin, polyamide, polyvinylidene-polyacrylonitrile, polyvinylidene-polyacrylonitrile-polymethylmethacrylate, polylactide coglycolide polymers (such as poly-d-L-lactide coglycolide polymers), nylon and polystyrene-polyacrylonitrile as well as polyfunctional cross-linking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof, as well as polyvinyls (such as, for example, polyvinyl alcohol (PVA), polyvinylchloride and polyvinylpyrrolidone), polystyrene, polylactic acids, fluorinated hydrocarbons, fluorinated carbons (such as, for example, polytetrafluoroethylene), and polymethylmethacrylate, and derivatives thereof. Also included are amphiphilic compounds composed of cationic polymers covalently modified with hydrophobic (e.g. lipid moieties as palmitoyl) and/or hydrophilic (polyethylene glycol) groups. The polymers may optionally be cross-linked, if desired, to enhance, for example, the stability of the nanoparticles. This could be achieved by cross linking cysteine-bearing polymers by oxidative polycondensation.

Examples of natural polymers include naturally occurring carbohydrates or polysaccharides, such as, for instance, polymers of or formed from arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, polydextrose, pustulan, chitin, chitosan, agarose, keratan, chondroitan, dermatan, hyaluronic acid, alginic acid, xanthan gum, starch, heparin (including, for example, heparin sulfate or heparitin sulfate), and various other natural homopolymer or heteropolymers, such as those containing one or more of the following aldoses, ketoses, acids or amines: erythrose, threose, ribose, arabinose, xylose, lyxose, allose, altrose, glucose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable natural polymers include, for example, proteins, such as albumin, collagen and gelatin. Examples of semi-synthetic polymers include carboxymethylcellulose, hydroxymethylcellulose, hydroxypropylmethylcellulose, methylcellulose, and methoxycellulose.

The residence time of the carrier (as well as of the microcapsules) in the systemic circulation can be adjusted (preferably increased) by incorporating suitable polymeric materials therein, including, for instance, polyethylenes (such as, for example, polyethylene glycol, polyoxyethylene, and polyethylene terephthlate), polypropylenes (such as, for example, polypropylene glycol), polyoxyethylene and polyoxypropylene copolymers, including polyoxyethylene and polyoxypropylene block copolymers, polyoxyalkylene derivatives of polyethylene glycol (such as, for example, the class of compounds referred to as Pluronics®, commercially available from BASF, Parsippany, N.J.).

As for lipoplexes, also polyplexes can be formulated as single entities or in more complex structures, such as micelles or liposomes. In addition to compositions formulated from lipids and or polymers, the methods of the present invention may also involve compositions and vesicles comprising cationic peptides such as KALA peptide (derived from the influenza HA-2 subunit), melittin, TAT. Furthermore, formulations comprising combinations of any of the above lipids and polymers are also foreseen. For instance, a gene carrier may include lipopolyplexes, where genetic material is condensed with a polycation and entrapped within anionic or neutral liposomes According to an alternative embodiment, said bioactive agent is a drug, including, for instance, antineoplastic agents such as vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (Lasparaginase), etoposide, interferon α-2a and 2b, blood products such as hematoporphyrins or derivatives of the foregoing; biological response modifiers such as muramylpeptides; antifungal agents such as ketoconazole, nystatin, griseofulvin, flucytosine, miconazole or amphotericin B; hormones or hormone analogues such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate; vitamins such as cyanocobalamin or retinoids; enzymes such as alkaline phosphatase or manganese superoxide dismutase; antiallergic agents such as amelexanox; anticoagulation agents such as warfarin, phenprocoumon or heparin; antithrombotic agents; circulatory drugs such as propranolol; metabolic potentiators such as glutathione; antituberculars such as p-aminosalicylic acid, isoniazid, capreomycin sulfate, cyclosexine, ethambutol, ethionamide, pyrazinamide, rifampin or streptomycin sulphate; antivirals such as acyclovir, amantadine, azidothymidine, ribavirin or vidarabine; blood vessel dilating agents such as diltiazem, nifedipine, verapamil, erythritol tetranitrate, isosorbide dinitrate, nitroglycerin or pentaerythritol tetranitrate; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin or tetracycline; antiinflammatories such as diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; antirheumatics such as penicillamine; narcotics such as paregoric; opiates such as codeine, morphine or opium; cardiac glycosides such as deslaneside, digitoxin, digoxin, digitalin or digitalis; neuromuscular blockers such as atracurium mesylate, gallamine triethiodide, hexafluorenium bromide, metocurine iodide, pancuronium bromide, succinylcholine chloride, tubocurarine chloride or vecuronium bromide; sedatives such as amobarbital, amobarbital sodium, apropbarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam; local anaesthetics such as bupivacaine, chloroprocaine, etidocaine, lidocaine, mepivacaine, procaine or tetracaine; general anaesthetics such as droperidol, etomidate, fentanyl citrate with droperidol, ketamine hydrochloride, methohexital sodium or thiopental and pharmaceutically acceptable salts (e.g. acid addition salts such as the hydrochloride or hydrobromide or base salts such as sodium, calcium or magnesium salts) or derivatives (e.g. acetates) thereof; and radiochemicals, e.g. comprising alpha-, beta-, or gamma-emitters such as, for instance $^{177}$Lu, $^{90}$Y or $^{131}$I.

The above drugs can be present as such in the composition of the invention or preferably they are associated with stabilizing components, to form e.g. micelles or liposomes. Examples of suitable compounds are phospholipids, including fatty acids di-esters of phosphatidylcholine, ethylphosphatidylcholine, phosphatidylglycerol, phosphatidic acid, phosphatidylethanolamine, phosphatidylserine or sphingomyelin; PEG-modified phospholipids, including in particular PEG-modified phosphatidylethanolamines; ammonium salts such as those previously listed comprising one or preferably two ($C_{10}$-$C_{20}$), preferably ($C_{14}$-$C_{18}$), acyl chain linked to the N-atom through a ($C_3$-$C_6$) alkylene bridge, such as 1,2-distearoyl-3-trimethylammonium-propane (DSTAP), 1,2-dipalmitoyl-3-trimethylammonium-propane (DPTAP), 1,2-dioleoyl-3-trimethylammonium-propane (DOTAP), 1,2-distearoyl-3-dimethylammonium-propane (DSDAP); fatty acid salts, preferably alkali, in particular sodium salts, such as sodium palmitate, sodium stearate, sodium oleate, sodium linoleate, sodium dodecanoate, 1,2-dipalmitoyl-sn-3-succinylglycerate sodium salt or 1,3-dipalmitoyl-2-succinylglycerol sodium salt. Polymeric surfactants can also be used, such as, for instance, polyethyleneoxides (PEO), such as ($C_8$-$C_{16}$) n-alkyl PEO monoether, ($C_8$-$C_{10}$)n-alkyl phenyl PEO, tetramethylbutylphenyl PEO, PEO polysorbates, these PEO being sold under commercial names of Brij®, Lubrol®, Triton®, Nonidet® or Tween®; block copolymers such as ethyleneoxide/propyleneoxide block copolymers (e.g. Pluronic® or Synperonic®), having preferably a MW of from about 3000 to 20000 daltons, preferably of from 5000 to 15000 daltons; sugar derivatives such as ($C_6$-$C_{10}$)alkyl-β-D-glucopyranoside, ($C_8$-$C_{12}$)alkyl-β-D-maltoside; ($C_8$-$C_{16}$) alkyldimethylammonium-propane-sulfonate; and bile acids and derivatives therof, such as sodium cholate or sodium deoxycholate.

According to a preferred embodiment of the invention, a drug can be locally delivered in combination with a genetic material, thus allowing a combined pharmaceutical/genetic therapy of the patient (e.g. in case of tumor treatment).

Whichever the carrier employed for associating the bioactive agent, it is important that a relevant portion of the resulting "bioactive carrier" (i.e. the carrier associated with the bioactive agent) is not stably incorporated into or associated with the envelope of the microcapsules, so that the larger amount of genetic material is free to penetrate into the cell after ultrasound application and microcapsules bursting.

Bioactive carriers are prepared as known in the art. Preferably, they are obtained as lyophilized materials, to be reconstituted before use with a suitable physiologically acceptable carrier.

For instance, bioactive carriers in the form of micelles can be prepared by dispersing the bioactive agent and the lipid or polymeric compound in an aqueous liquid carrier and optionally agitating the mixture. Examples of suitable liquid carriers are water, saline solution (sodium chloride 0.9%), Phosphate buffered saline (10 mM, pH 7.4), HEPES buffer (20 mM, pH 7.4), Glucose 5% w/w in water. For instance, the above compounds can be dispersed in a concentration of from about 1 to 100 mg/ml in an aqueous liquid and dissolved by means of agitation or sonication.

The micelles can then be stored as an aqueous dispersion (e.g. in the aqueous carrier used for their preparation) before being administered or admixed with a suspension containing microcapsules. Alternatively, the micelle suspension can be freeze-dried according to conventional techniques, to eliminate the liquid and store the final dry product for the subsequent uses.

The above carriers can further be modified to include a suitable targeting ligand. This further modification allows the carrier bearing the bioactive agent to selectively bind to a desired cell, tissue or organ to which the bioactive agent will be delivered.

The term "targeting ligand" includes within its meaning any compound, moiety or residue having, or being capable to promote, a targeting activity of the carrier comprising the genetic material towards any biological or pathological site within a living body. Targets to which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, immunoglobulins and cytoplasmic receptors for steroid hormones.

Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

Examples of suitable targets and targeting ligands are disclosed, for instance, in U.S. Pat. No. 6,139,819, which is herein incorporated by reference.

The targeting ligand can be a compound per se which is admixed with the other components of the carrier or can be a compound which is bound to a molecule included in the carrier.

In one preferred embodiment, the targeting ligand can be bound to a molecule of the carrier through a covalent bond. In such a case, the specific reactive moiety that needs to be present on the molecule will depend on the particular targeting ligand to be coupled thereto. As an example, if the targeting ligand can be linked to the molecule through an amino group, suitable reactive moieties for the molecule may be isothiocyanate groups (that will form a thiourea bond), reactive esters (to form an amide bond), aldehyde groups (for the formation of an imine bond to be reduced to an alkylamine bond), etc.; if the targeting ligand can be linked to the molecule through a thiol group, suitable complementary reactive moieties for the molecule include haloacetyl derivatives or maleimides (to form a thioether bond); and if the targeting ligand can be linked to the molecule through a carboxylic group, suitable reactive moieties for the molecule might be amines and hydrazides (to form amide or alkylamide bonds). In order to covalently bind a desired targeting ligand, at least part of the compounds forming the carrier shall thus contain a suitable reactive moiety and the targeting ligand containing the complementary functionality will be linked thereto according to known techniques, e.g. by adding it to an aqueous dispersion comprising the suitable components of the carrier. The compound can be combined with the desired targeting ligand before preparing the carrier, and the so obtained combination can be used in the preparation process of the carrier. Alternatively, the targeting ligand can be linked to the respective compound during the preparation process of the carrier or can be directly linked to the compound already incorporated into the carrier.

According to an alternative embodiment, the targeting ligand may also be suitably associated with the carrier via physical and/or electrostatic interaction. As an example, a functional moiety having a high affinity and selectivity for a complementary moiety can be introduced into a molecule of the carrier, while the complementary moiety will be linked to the targeting ligand. For instance, an avidin (or streptavidin, neutravidin or Extravidin®) moiety (having high affinity for biotin) can be covalently linked to a phospholipid while the complementary biotin moiety can be incorporated into a suitable targeting ligand, e.g. a peptide or an antibody. The biotin-labelled targeting ligand will thus be associated with the avidin-labelled phospholipid of the carrier by means of the avidin-biotin coupling system. Alternatively, both the phospholipid and the targeting ligand can be provided with a biotin moiety and subsequently coupled to each other by means of avidin (which is a bifunctional component capable of bridging the two biotin moieties). Examples of biotin/avidin coupling of phospholipids and peptides are also disclosed in the above cited U.S. Pat. No. 6,139,819. Alternatively, van der Waal's interactions, electrostatic interactions and other association processes may associate or bind the targeting ligand to the desired molecules.

According to an alternative embodiment, the targeting ligand can be a compound which is admixed with the components forming the carrier, to be eventually incorporated into the carrier, such as, for instance, a lipopeptide as disclosed e.g. in International patent Applications WO 98/18501 or 99/55383, both herein incorporated by reference.

Alternatively, a carrier can first be manufactured, which comprises a compound having a suitable moiety capable of interacting with a corresponding complementary moiety of a targeting ligand; thereafter, the desired targeting ligand is added to a suspension of the carrier, to bind to the corresponding complementary moiety on the carrier.

Examples of suitable specific targets to which the assembly can be directed are, for instance, fibrin and the GPIIbIIIa binding receptor on activated platelets. Fibrin and platelets are in fact generally present in "thrombi", i.e. coagula which may form in the blood stream and cause a vascular obstruction. Suitable binding peptides are disclosed, for instance, in the above cited U.S. Pat. No. 6,139,819. Further binding peptides specific for fibrin-targeting are disclosed, for instance, in International patent application WO 02/055544, which is herein incorporated by reference.

Other examples of important targets include receptors in vulnerable plaques and tumor specific receptors, such as kinase domain region (KDR) and VEGF (vascular endothelial growth factor)/KDR complex. Binding peptides suitable for KDR or VEGF/KDR complex are disclosed, for instance, in International Patent application WO 03/74005 and WO 03/084574, both herein incorporated by reference. Other examples of tumor specific ligands are, for instance, transferrin, folic acid, arginine-glycine-aspartic acid sequence (RGD), NRG sequence (for targeting aminopeptidase expressed on newly formed vessels) or GA3 peptide sequence (target Tie2 receptor involved in tumor angiogenesis).

The composition of the invention can further contain, if desired, a diagnostic agent, which can be also incorporated in the above carrier or provided as a separate entity.

The term "diagnostic agent" includes within its meaning any compound, composition or particle which may be used in connection with diagnostic methods, including imaging of an internal region of a patient and/or diagnosing the presence or absence of a disease in a patient. Exemplary diagnostic agents include, for example, contrast agents for use in connection with ultrasound imaging (e.g. gas-filled microbubbles), magnetic resonance imaging, X-ray imaging, in particular computed tomography, optical imaging, nuclear imaging or molecular imaging of a patient including, for example, magnetite nanoparticles. A diagnostic agent can be useful, for instance, to identify the exact location where ultrasound waves are to be applied for determining an effective delivery of the bioactive agent.

The composition of the invention can further contain suitable adjuvants for further enhancing the delivery of the bioactive agent, in particular of genetic material, into cells. Useful adjuvants include polyoxyalkylene fatty acid esters (such as polyoxyethylene fatty acid esters), polyoxyalkylene fatty alcohols (such as polyoxyethylene fatty alcohols), polyoxyalkylene fatty alcohol ethers (such as polyoxyethylene fatty alcohol ethers), polyoxyalkylene sorbitan fatty esters (such as, for example, the class of compounds referred to as TWEEN™, commercially available from ICI Americas, Inc., Wilmington, Del.), polyethylene glycol (PEG) of various molecular weights, poly(oxyethylene)-poly(oxypropylene) copolymers (such as Pluronics®, Synperonic®) preferably with an hydrophilic-lipophilic balance (HLB) superior to 10 (e.g. Pluronic F68, F127 or F85), polysorbates (such as Tween20, Tween40, and Tween80), polyoxyethylene alcohols (such as Brij), and plasmalogens, the term applied to a group of phospholipids present in platelets that liberate higher fatty aldehydes, e.g. palmital. Local anesthetics such as lidocaine, ropivacaine, bupivacaine, mepivacaine, as well as phenobarbital or pentobarbital are also known to increase membrane fluidity and might further improve gene delivery upon insonation. Derivatives of 1-4 dihydropyridine may also be used (e.g. hexadecyl 4-beta pyridyl) as well as alkyl glycosides and alkyl polyglycosides derivatives.

The composition of the invention can be formulated in a variety of ways, in order to be administered in a method for effectively delivering a bioactive agent into a cell.

For instance, the composition can be obtained by admixing an aqueous suspension comprising the microcapsules (obtained according to any of the above cited manufacturing methods) with an aqueous suspension comprising the bioactive agent, preferably associated with a suitable carrier. The products are in fact readily reconstitutable in a suitable aqueous liquid carrier, which is physiologically acceptable, sterile and injectable, to form the gas-filled microvesicles. Suitable liquid carriers are water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like). If desired, suitable additives can be added to the formulation, such as, for instance, the previously mentioned adjuvants.

Upon formation, the suspension comprising the composition of the invention can be stored for a subsequent administration or can be directly administered. If desired, the liquid carrier of the suspension can be eliminated (e.g. by freeze-drying) to obtain a dry powder of the composition which can be stored (preferably in the presence of a gas suitable for forming the gas-filled microcapsules upon reconstitution) for relatively long periods of time before reconstitution.

Alternatively, the components of the composition can be stored as separate compositions in dried form (e.g. freeze dried) and reconstituted as a suspension before administration. For the storage, the dried components are preferably kept in an atmosphere of the gas which will form the microcapsules upon reconstitution. The reconstitution with an aqueous liquid carrier may take place separately on the two dried compositions comprising the respective components, thus obtaining two separate suspensions. These can then be administered separately or admixed before administration. According to a preferred embodiment, a suspension of the dried bioactive agent is used for reconstituting the dried microcapsules composition, to finally obtain a suspension of the composition. Optionally, the freeze-dried bioactive agent (preferably associated with a carrier) is first reconstituted with a physiologically acceptable aqueous carrier and the obtained suspension is then used for reconstituting the dried microcapsules composition.

Injectable compositions (also after reconstitution of the lyophilised composition) should be, as far as possible, isotonic with blood. Hence, before injection, small amounts of isotonic agents may also be added to the suspensions comprising the assembly of the invention. The isotonic agents are physiological solutions commonly used in medicine such as, for example, aqueous saline solution (0.9% NaCl), 2.6% glycerol solution or 5% dextrose solution. The reconstitution of the aqueous suspensions is generally obtained by simple dissolution of the gas-stored dried film forming surfactant and gentle agitation.

The volume and concentrations of the reconstitution liquid may desirably be balanced to make the resulting ready-to-use formulations substantially isotonic. Hence the volume and concentration of reconstitution fluid chosen will be dependent on the type and amount of stabilizer (and other bulking agents) present in the freeze-dried product.

The present invention is also directed to a pharmaceutical kit which comprises microcapsules and a bioactive agent, as above defined. The components can be mixed together or separately provided in the kit, either as suspensions or as freeze-dried components. Preferably both components are provided in freeze-dried form, for instance in separate containers, such as separate vials or packets. The kit can thus further comprise a suitable physiologically acceptable aqueous carrier, such as those previously listed, for reconstituting the freeze-dried components (either separately or in a single suspension). The pharmaceutical kit may further comprise conventional kit components known to those skilled in the art once armed with the present disclosure, such as, mixing vials, syringes, needles.

The useful dosage of microcapsules and bioactive agent to be administered or delivered, as well as the mode of administration, will vary depending upon type and nature of the compound to be delivered, the age, weight, cells of patient (animal) to be treated, the particular diagnostic, therapeutic, or other application intended (including the disease state, if any, to be treated), and carrier (if any) employed. Typically, dosage is initiated at lower levels and may be increased until the desired therapeutic effect is achieved. The microcapsules and the bioactive agent of a composition of the invention can be administered either concurrently (e.g. in a same physiologically solution), or at subsequent times, thus forming the composition of the invention at the desired location where ultrasounds are applied. In this latter case, the bioactive agent can be administered first, in order to allow sufficient time for it to circulate and/or to bind to the desired target (in case it is associated with a targeted carrier). Alternatively, the microcapsules can be administered first, followed by the administration of the bioactive agent.

Those skilled in the art, based on the present description and on general medical literature will be able to set the desired dosage, including any therapeutically effective dosage amounts.

The composition of the invention can be administered in various ways, also depending on its specific formulation. Examples of suitable administrations are, for instance, intravascularly, intralymphatically, parenterally, subcutaneously, intramuscularly, intradermally, intraperitoneally, interstitially, intrathecally, intranasally, via nebulizer into the airways, occularly, orally, intrarectally, topically, or intratumorally, using a variety of dosage forms. One method of topical administration is the injection of a nucleotide sequence (or other compound to be delivered), by a porous balloon catheter (SCIMED Remedy, Boston Scientific, Natick, Mass.) or a needle injection catheter (Boston Scientific, Natik, Mass.). The balloon catheter (containing channels) is inserted into the blood stream of a patient. Once the balloon of the catheter reaches the location to which the bioactive agent is to be administered, the balloon is pumped up then a mixture of microcapsules and bioactive agent is infused through the channel thus delivering the composition to the vessel wall. Ultrasound is then applied to the desired location, either internally (for instance endoscopically or intravascularly) or externally. A second drug delivery catheter, is based on needle injection catheter, enabling direct administration of microcapsules/bioactive agent into the desired location, then followed by ultrasound exposure as described above.

"Ultrasound", "Ultrasound applications", and similar terms, refer to waves of sound energy, preferably transmitted in a repetitive way, sufficient to induce substantial bursting of gas-filled microcapsules and assist the delivery of a bioactive agent into a cell. Preferably, the ultrasound is in the frequency range of from about 20 kHz to less than about 50 MHz, with an energy level (also referred to as spatial-peak time-average intensity, $I_{spta}$) of from about 0.5 mW/cm$^2$ to about 10 W/cm$^2$. For the specific method of the invention, said ultrasound will preferably have an acoustic pressure of at least 200 kPa at a frequency of 1.15 MHz, or at least 300 kPa at a frequency of 2.25 MHz, up to e.g. 10 MPa. Typically the ultrasound is applied by external application, by means of conventional clinical ultrasound devices or a single element transducer, but may also be applied internally, such as endoscopically and intravascularly as described above.

Typically, higher energy levels and lower ultrasonic frequencies are required for penetration into deep seated tissues; lower energy levels and higher ultrasonic frequencies may be used for treatment of superficial tissues or when the ultrasound transducer can be applied directly to the tissue surface. For in vitro applications, the volume and geometry of the container containing the cell culture may affect the choice of energy and frequency. For instance, small volume cell culture samples may need less energy for ultrasound enhanced transfection than large volume bioreactor chambers.

For intravascular applications, which may employ intravascular catheters equipped with ultrasound transducers for endovascular gene therapy, higher frequencies may be employed such as over about 10 MHz. For most applications however the frequency of the sound ranges from about 300 kHz to about 3 MHz, preferably from about 500 kHz to about 1.5 MHz, more preferably about 1 MHz. Typically, ultrasound for use in the present invention is provided at a frequency lower than the conventional frequency used for imaging applications.

Typically, the energy level settings can be higher than those employed in diagnostic ultrasound, ranging from 0.5 mW/cm$^2$ to about 10 W/cm$^2$, preferably from about 1 mW/cm$^2$ to about 3 W/cm$^2$. The energy level which is applied is selected so that the total energy deposition is generally below the cytotoxic threshold for the cells or tissue.

Generally, frequencies and energy levels are applied at lower amounts, and then increased until the desired cellular uptake of the administered compound is achieved.

The ultrasound energy is applied in periods which are defined by a given duty cycle. Generally continuous wave ultrasound which applies a constant exposure of ultrasound energy (duty cycle of 100%) is employed. The duty cycle is selected so that the level of energy output is in a desired range. The duty cycle may be adapted to the application and can be varied over a wide range of values (e.g. 0.1%-100%).

While high energy levels of ultrasound may be used for hyperthermia to heat the tissue and also to directly ablate tissues, in the method of the invention, energy levels are generally far below those which cause tissue ablation and below those which cause a significant hyperthermic effect. While the application of ultrasound energy necessary to increase the efficiency of delivery of bioactive agent may result in a few degrees centigrade increase in temperature, any increase in temperature is typically transient and the temperature rapidly returns to baseline. Preferably the temperature does not increase significantly during application of the ultrasound, any increase in temperature being typically less than about 1° C. to about 2° C. Progressively higher levels of ultrasound energy will result in progressive rises in temperature but temperature is preferably maintained below the level where significant cytotoxicity will occur (e.g. 44° C. or higher). The amount of energy and/or the time of exposure may be modified so as to prevent temperature-induced cell destruction. Some applications may however benefit from a certain degree of hyperthermia, such as, for instance, in the case of cancer therapy where combination of ultrasound-mediated delivery and hyperthermia may improve treatment by enabling killing of a portion of tumor cells by hyperthermic effect.

The ultrasound energy may be applied to the tissue or cells after injection of microcapsules, simultaneously with or after administration of the bioactive agent to the cell. Typically the ultrasound energy is applied after injection of microcapsules and no more than about 48 hours after the bioactive agent has been administered, although longer or shorter times may be applied.

Either one or multiple exposures of ultrasound energy may be employed. The duration of ultrasound exposure (exposure time) will vary depending upon the energy level of the ultrasound and the duty cycle. To determine the preferable duration, ultrasound is typically applied at lower exposure times, and increased until the desired cellular uptake of the compound administered is achieved. A high energy level (typically greater than about 2 W/cm$^2$, preferably over about 5 W/cm$^2$, and also preferably over about 10 W/cm$^2$, depending on the duty cycle) ultrasound shock wave may require only a few milliseconds of exposure time. More typically the exposure time ranges from about a few seconds to up to about an hour of ultrasound energy exposure to the cell to achieve most effective ultrasound enhanced delivery of the bioactive agent. Even more preferably the duration of ultrasound exposure ranges from about a few seconds to about a few minutes and may be repeated at various intervals during transfection. The duration of ultrasound energy exposure should be sufficient to cause the desired effect but not so long that significant cytotoxicity (unless expressly required) may result.

The ultrasound energy may be applied with any of a variety of commercially available ultrasound systems. For example a Rich-Mar model Sonitron 2000 ultrasonic therapy apparatus (Inola, Okla.) with the center frequency of approximately 1 MHz, in pulsed or continuous mode, may be used. Conventional transducers, power amplifiers and other component systems for practicing the invention can also be readily assembled. Alternatively, a pulse/function generator or an arbitrary function Tabor 8024 (Tabor electronics Ltd, Hanan, Israel) may also be incorporated into the system to allow control over the pulse repetition intervals, duty cycles, etc. If desired, specific frequency and amplitude effects such as, for instance CHIRP (increasing in frequency) and PRICH pulses (decreasing in frequency) waveform patterns can be obtained by modifying the ultrasound. Ultrasonic energies can also be supplied from commercially available amplifiers, transducers and frequency generators. By way of example, a power transducer with a center frequency of 1.15 MHz from Valpey-Fisher (Valpey-Fisher, Hopkinton, Mass.), a power RF amplifier from ENI (ENI, Rochester, N.Y.), and an arbitrary function generator Tabor 8024 (Hanan, Israel) may be a suitable setup. Alternatively, a power transducer from Panametrics (Panametrics V304) with a center frequency of 2.25 MHz can also be used in the setup. Finally ultrasound energy may be applied through diagnostic ultrasound equipments.

The high energy ultrasound system may also be incorporated with a conventional ultrasound imaging system to allow imaging and therapeutic application of ultrasound with the same apparatus.

Alternatively, the application of high energy ultrasound may also be performed in combination with other forms of conventional imaging such as endoscopy (e.g. fiber-optic), computed tomography, magnetic resonance imaging, angiography, and nuclear medicine.

Any associated imaging technique may be employed, for example, to locate and identify in a patient the cells (located e.g. in a tissue or organ) to which the high energy ultrasound should be applied, or used to follow and/or locate the composition of the invention after administration to a patient.

The following examples will illustrate the invention more in detail.

EXAMPLES

Example 1

Preparation of Thin-Shell Microbubbles Filled with Air (Comparative)

A solution containing 15 mg of distearoyl phosphatidylcholine (DSPC), 15 mg of dipalmitoyl phosphatidylglycerol (DPPG) and 3 mg of palmitic acid in hexane/ethanol 8/2 (v/v) is prepared and the solvent evaporated to dryness. The resulting powder and 2 g of polyethylene glycol (MW4000) are dissolved in 14 g of tert-butanol at 60° C. The solution is aliquoted in 10 ml glass vials (250 µl/vial), rapidly cooled to −45° C. and lyophilised. The lyophilisate is exposed to air and then reconstituted with 5 ml of 0.9% saline solution by gentle swirling. The resulting suspension contains air-filled microbubbles (2×10$^8$ bubbles/ml, analysed by Coulter Multisizer II).

Example 2

Preparation of Thin-Shell Microbubbles Filled with Perfluorocarbon (Comparative)

The procedure of Example 1 is repeated except that the air in glass vial containing the lyophilisate was first evacuated by a vacuum pump and replaced by a perfluorocarbon gas ($C_4F_{10}$). The stiffness of the obtained microbubbles, measured according to the previously described methodology, is of about 1 N/m.

Example 3

Preparation of Lipid-Shell Microcapsules Filled with Air 60 mg of tripalmitin is dissolved in cyclohexane (0.6 ml). Distearoyl phosphatidylglycerol, sodium salt (DSPG.Na—40 mg) is dispersed in distilled water (30 ml) at 70° C. for 20 minutes and cooled to 45° C. The organic phase is emulsified in the aqueous phase using a POLYTRON® homogeniser (8500 rpm). The average diameter of the resulting droplets is of about 3 μm as determined with a photon correlation spectrometer (Malvern Master Sizer®).

This emulsion was added to a 500 ml glass vessel containing 200 mg of polyvinyl alcohol (PVA—MW 9000—from Aldrich) dissolved in 5 ml of distilled water. After mixing, the resulting emulsion was rapidly frozen at −40° C. and lyophilised (Christ Beta 1-8K).

The cake was resuspended in 20 ml of water. Air-containing microcapsules rose to the surface. The floating capsules were recovered, resuspended in 0.9% NaCl and analyzed with a Coulter counter Multisizer II. The stiffness of the obtained microcapsules, measured according to the previously described methodology, was higher than 50 N/m.

Example 4

Preparation of Lipid-Shell Microcapsules Filled with Perfluorocarbon Gas

Example 3 is repeated except that air in the glass vial containing the lyophilisate is first evacuated by a vacuum pump and the lyophilisate is exposed to perfluorobutane in order to generate $C_4F_{10}$-containing microcapsules. The stiffness of the obtained microcapsules, measured according to the previously described methodology, was higher than 50 N/m.

Example 5

Preparation of Polymer-Shell Microcapsules 40 mg of 30 kDa MW polystyrene (Standard MW 30,000, Fluka Chemie) are dissolved in cyclohexane (1 ml). Distearoyl phosphatidylglycerol, sodium salt (DSPG.Na—40 mg) is dispersed in distilled water (30 ml) at 70° C. for 20 minutes and cooled to 45° C. The organic phase is emulsified in the aqueous phase using a POLYTRON® homogeniser (13'000 rpm, Kinematica, Switzerland).

The emulsion is added to a 500 ml glass vessel containing 200 mg of polyvinyl alcohol (PVA—MW 9000—from Aldrich) dissolved in 5 ml of distilled water. After mixing, the resulting emulsion is rapidly frozen at −40° C. and lyophilised. The cake is resuspended in 20 ml of water. Air-containing microcapsules rise to the surface. The floating capsules are recovered, resuspended in 0.9% NaCl solution containing 0.05% of Pluronic F68 and analyzed with a Coulter counter Multisizer II. The stiffness of the obtained microcapsules, measured according to the previously described methodology, was of about 8 N/m.

Example 6

Preparation of Polymer-Shell Microcapsules

Example 5 is repeated by replacing the 30 kDa MW polystyrene with the same amount of 100 kDa polystyrene. The stiffness of the obtained microcapsules, measured according to the previously described methodology, was of about 12 N/m.

Example 7

Preparation of Polymer-Shell Microcapsules

Example 5 is repeated by replacing the 30 kDa MW polystyrene with the same amount of 300 kDa polystyrene. The stiffness of the obtained microcapsules, measured according to the previously described methodology, was of about 15 N/m.

Example 8

Preparation of Targeted Micelle Complex Containing a Plasmid

Cationic micelles are prepared with 1 mg/ml of cationic phospholipid DPEPC (Dipalmitoyl Glycero-3-Ethylphosphocholine, Avanti® Polar Lipids, Inc. USA), 4 mg/ml of DSPE-PTE020 (a multi-arm PEG-phospholipid, NOF Corporation, Japan), and 0.25 mg/ml of maleimide-PEG2000-distearoylphosphatidylethanolamine (Shearwater Polymer, Ala., USA).

These compounds are first dissolved in chloroform:methanol (2:1, v/v) in a round-bottom flask and the solvents are then evaporated under reduced pressure to obtain a lipid film. Cationic micelles are obtained by hydration of the lipid film in 10 mM HEPES buffer at 60° C.

Acetylthioacetyl RGD-peptide (a peptide with affinity for Alpha v beta 3-integrins expressed in tumour angiogenesis) is deacetylated in an aqueous solution of 0.05 M HEPES/0.05 M hydroxylamine-HCl/0.03 mM EDTA at pH 7 for 30 min at room temperature. The activated RGD peptide is incubated overnight at 4° C. with the micelles at a peptide-to-maleimide molar ratio of 1:2. The resulting RGD-micelles are purified on a Sephadex G-100 column using HEPES buffer as eluent.

Plasmid gWiz®-GFP (5757 base pairs; Aldevron, Fargo, USA), encoding for the green fluorescent protein at 100 μg/ml in Hepes buffer is added to RGD-cationic micelles to obtain targeted plasmid containing micelle complex, which can be used in combination with the above described microcapsules in a composition according to the invention.

Example 9

Preparation of Targeted Microcapsules

Preparation of RGD-PEG2000-DSPE

Acetylthioacetyl RGD-peptide (a peptide with affinity for Alpha v beta 3-integrins expressed in tumour angiogenesis) is deacetylated in an aqueous solution of 0.05 M HEPES/0.05 M hydroxylamine-HCl/0.03 mM EDTA at pH 7 for 30 min at room temperature. The activated RGD peptide is incubated overnight at 4° C. with maleimide-PEG2000-DSPE solution at a peptide-to-maleimide molar ratio of 1:2. The resulting RGD-PEG2000-DSPE is purified on a Sephadex G-100 column using HEPES buffer as eluent.

Preparation of RGD-Containing Targeted Microcapsules 60 mg of tripalmitin is dissolved in cyclooctane (0.6 ml). 5 mg of RGD-PEG2000-DSPE and 40 mg of DSPG.Na are dispersed in distilled water (30 ml) at 70° C. for 20 minutes and cooled to 45° C. The organic phase is emulsified in the aqueous phase using a POLYTRON® homogenizer (8500 rpm).

The resulting micro-emulsion is centrifuged to remove excess lipids (tripalmitin, DSPG and RGD-PEG2000-DSPE) and then added to a 500 ml glass vessel containing 40 mg/ml of polyvinyl alcohol (PVA) aqueous solution. The emulsion is finally frozen at −40° C. and lyophilized. RGD-peptide containing microcapsules were finally obtained by reconstitution of lyophilized cake with saline solution.

Example 10

RGD-containing targeted microcapsules are prepared as described in Example 9, except that the RGD-PEG2000-DSPE is dissolved in the organic phase (cyclooctane) instead of in the aqueous phase (DSPG.Na water suspension).

Examples 11-15

In Vitro Gene Delivery Experiments

Protocol for Gene Delivery Tests

The gene delivery tests are performed in 3 mL sample tubes containing a cell suspension with a plasmid expressing a fluorescent protein, to which different formulations of gas-filled microvesicles (microbubbles or microcapsules), prepared according to the above examples, are added.

Rat mammary adenocarcinoma cells MAT B III (#CRL-1666 from ATCC) are incubated at 37° C. under 5% $CO_2$ atmosphere, in 225 $cm^2$ tissue culture flasks, in the Mac Coy's 5A medium containing Glutamax-I (Life Technologie, Switzerland), supplemented with 10% v/v heat-inactivated foetal calf serum (FCS) and 1% v/v antibiotics (initial concentration: 10,000 IU/ml Penicillin, 10,000 µg/mL Streptomycine, 25 µg/mL Fungizone).

Each tube contains a 500 µl cell suspension, at a final concentration of $1 \times 10^6$ cells/ml, which is mixed with a culture medium (Mac Coy's A medium, Life Technologie, Switzerland) containing the plasmid gWiz®-GFP (Aldevron, Fargo, USA), encoding for the green fluorescent protein (GFP).

Gene delivery assays are performed with a plasmid concentration of 10 µg/mL and a microvesicles/cell ratio of 30. The tube is mounted on a rotating exposure system and immersed in a water bath of 37° C. (D. L. Miller, S. Bao, J. E. Morris, Sonoporation of cultured cells in the rotating tube exposure system, Ultrasound in Med. Biol., 25, 1, (1999) 143-149). The distance between the transducer and the tube is 7.6 cm. The tubes are insonated for 10 seconds, using two different transducers (T1 or T2) characterized as follows:

| | Manufacturer | Operating Frequency [MHz] | Type | Aperture [mm] | Near field distance [mm] |
|---|---|---|---|---|---|
| T1 | Valpey Fisher | 1.15 | Unfocused/ air-backed | 19.1 | 76 |
| T2 | Panametrics V304 | 2.25 | Focused | 25.4 | 76 |

Insonation of cell suspension is performed according to the following parameters: duty cycle of 20%, pulse repetition frequency of 100 Hz, and at acoustic pressures as indicated in the specific examples. The ultrasound delivery system further comprises a power RF amplifier ENI A150 (ENI, Rochester, N.Y.), and an arbitrary waves generator Tabor 8024 (Tabor Electronics Ltd, Hanan, Israel).

The values of acoustic pressure (peak negative) indicated in the following examples are measured following a standard calibration procedure using a calibrated membrane hydrophone (membrane hydrophone, #MH026, Precision Acoustic Ltd, Dorshester, England).

After insonation, the respective mixtures are transferred from the tube into 12-well plates and supplemented with 2 mL of medium containing 10% FCS. Then cells are incubated at 37° C. in a 5% $CO_2$ atmosphere for 24 hours.

The cells are then analysed with a FACS Calibur (Becton dickinson AG, Switzerland) to determine the percentage of GFP-positive cells and the mean fluorescence intensity of positively transfected cells. Briefly, culture medium and cells are placed in a 5 mL polystyrene tube 24 hours after transfection, washed with phosphate buffer saline (PBS), then resuspended in 300-400 µL PBS and kept on ice. GFP is excited using the 488 nm line of an Argon laser, and emitted light is collected at 520 nm (green fluorescence) and 575 nm (red fluorescence) to enable correction for autofluorescence by diagonal gating. Prior to measurement, propidium iodide (20 µL from a 40 µL/mL solution) is added to the tube to determine the cell viability. Background fluorescence is determined using mock transfected cells (i.e. cells exposed to ultrasound in absence of plasmid DNA and microvesicles). The software program CellQuest Pro is used to analyse data to express the percentage of GFP-positive cells and the mean fluorescence intensity (arbitrary unit, AU). The percentage of GFP-positive cells (which indicates the amount of cells which have been positively transfected) relates to the whole cell population, including dead cells; however, debris from cells destroyed by ultrasound are not taken into account. The mean fluorescence intensity measured is proportional to the amount of GFP produced by the cell upon transfection (and thus in turn proportional to the number of plasmid copies which have been effectively delivered into the cell).

Example 11

Gene Delivery by Insonation in the Presence of Microcapsules or Microbubbles

Four aliquots of the microbubbles formulations prepared according to example 1 are added to respective sample tubes containing the suspension of cells and plasmid as above described and insonated with transducer T2 at respective acoustic pressures of 247 KPa, 364 KPa, 571 KPa and 808 KPa. The measured percentage of GFP-positive cells (% GFP-positive cells) and mean fluorescence intensities of positive cells are reported in FIGS. 1a and 1b, respectively, as black circles.

Similarly, four aliquots of the microcapsules formulations prepared according to example 3, are added to respective sample tubes containing the suspension of cells and plasmid as above described and insonated with the same transducer T2 at the same respective different acoustic pressures.

Figure 1B:
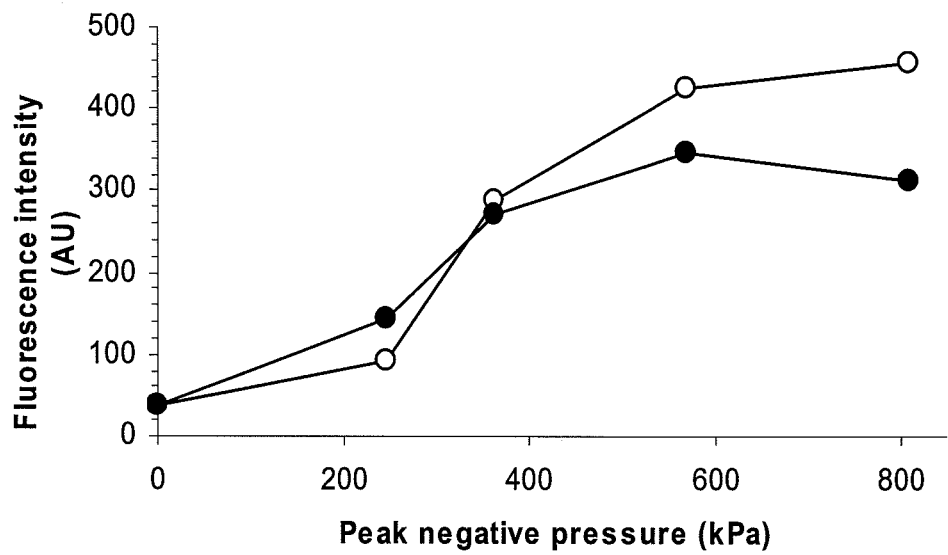

The measured % of GFP-positive cells and fluorescence intensities of positive cells are reported in FIGS. 1a and 1b, respectively, as white circles.

As observed from these figures, the maximum % of GFP-positive cells is of about 25% for microbubbles (at 364 kPa) and of about 17% for microcapsules (at 808 kPa). However, cells insonated in the presence of microcapsules show a higher value of mean fluorescence intensity (about 440 AU at 808 kPa) with respect to cells insonated in the presence of microbubbles (about 340 AU at 571 KPa). Thus, notwithstanding a slightly lower amount of transfected cells, microcapsules allow a more effective transfer of bioactive agent into the cells. In the practice, a lower number of cells are transfected upon insonation in the presence of microcapsules, but a higher concentration of bioactive agent is nevertheless delivered into the cells.

Example 12

Gene Delivery by Insonation

Microcapsules Vs. Microbubbles

Example 11 is repeated, by comparing the microbubbles of example 2 with microcapsules of example 4, with the same modality. In addition, transducer T1 (focused, 1.15 MHz) is employed instead of T2, at respective acoustic pressures of 207 kPa, 307 kPa, 402 kPa and 480 kPa. The results (% of GFP-positive cells and mean fluorescence intensities) are shown in FIGS. 2a and 2b (black circles: microbubbles; white circle: microcapsules).

Figure 2A:
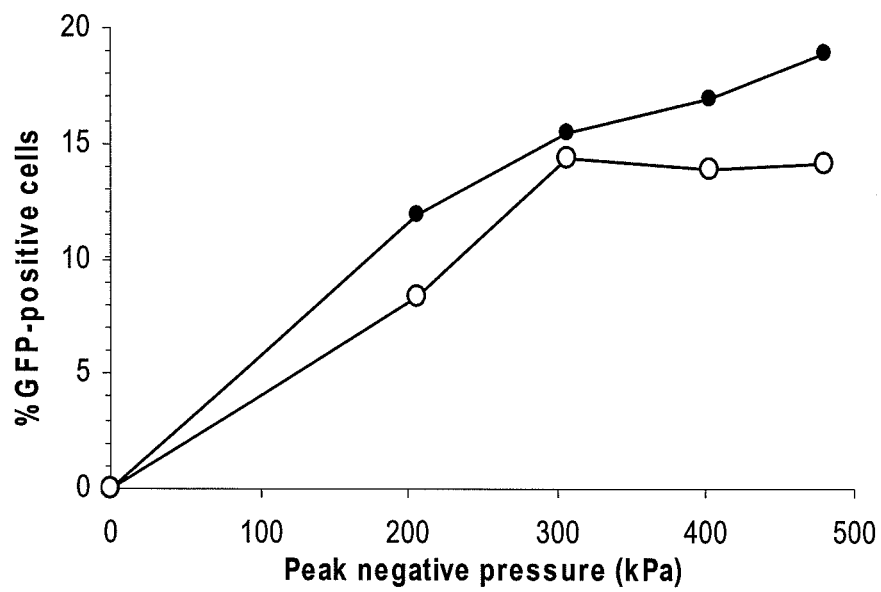
FIGS. 2a and 2b show the % of GFP-positive cells and the mean fluorescence intensities of positive cells measured upon ultrasound mediated gene delivery by using compositions containing microbubbles or microcapsules, at 1.15 MHz.
Figure 2B:
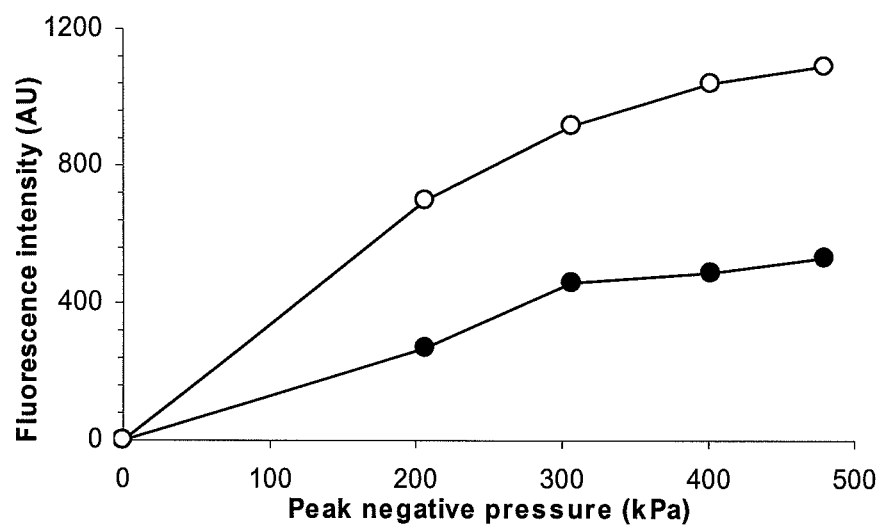

As observed from FIG. 2a, the maximum % of GFP-positive cells is of about 18.5% for microbubbles and of about 14% for microcapsules. According to FIG. 2b, it can be observed that cells insonated in the presence of microcapsules show a much higher value (almost double) of mean fluorescence intensity with respect to cells insonated in the presence of microbubbles (i.e. about 1120 AU as compared to about 550 AU, at 480 KPa).

Example 13

Gene Delivery by Insonation with Polymeric Microcapsules

Effect of Molecular Weight

Figure 3:
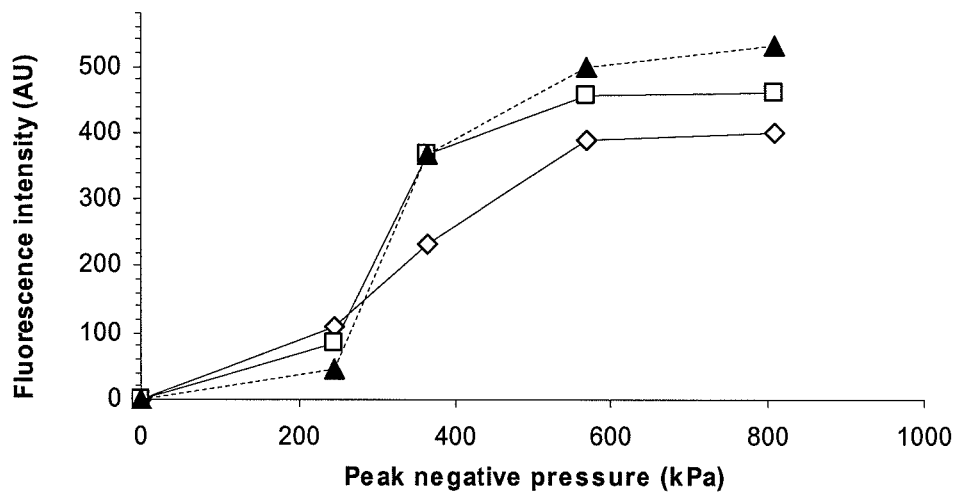
FIG. 3 shows the mean fluorescence intensities of GFP-positive cells measured upon ultrasound mediated gene delivery by using compositions containing microcapsules made from polymers of different molecular weights.

Four aliquots of each of the three formulations prepared according to examples 5, 6 and 7, respectively, are added to respective polystyrene tubes containing the suspension of cells and plasmid as described above and insonated with transducer T2 at respective acoustic pressures of 247 KPa, 364 KPa, 571 KPa and 808 KPa. The measured mean fluorescence intensities (determined as above described) are reported in FIG. 3 (Example 5: white diamonds; example 6: white squares; example 7: black triangle). From FIG. 3, it can be observed that the cells insonated in the presence of microcapsules made of higher molecular weight polymer, particularly at acoustic pressures higher than 400 KPa, show higher mean fluorescence intensities, corresponding to a more effective delivery of the plasmids into the cells.

Example 14

Gene Delivery by Insonation

Effect of Filling Gas

Four aliquots of each of the formulations prepared according to example 3 or example 4 were added to respective polystyrene tubes containing the suspension of cells and plasmid as above described and insonated with transducer T2 at respective acoustic pressures of 247 KPa, 364 KPa, 571 KPa and 808 KPa.

Figure 4:
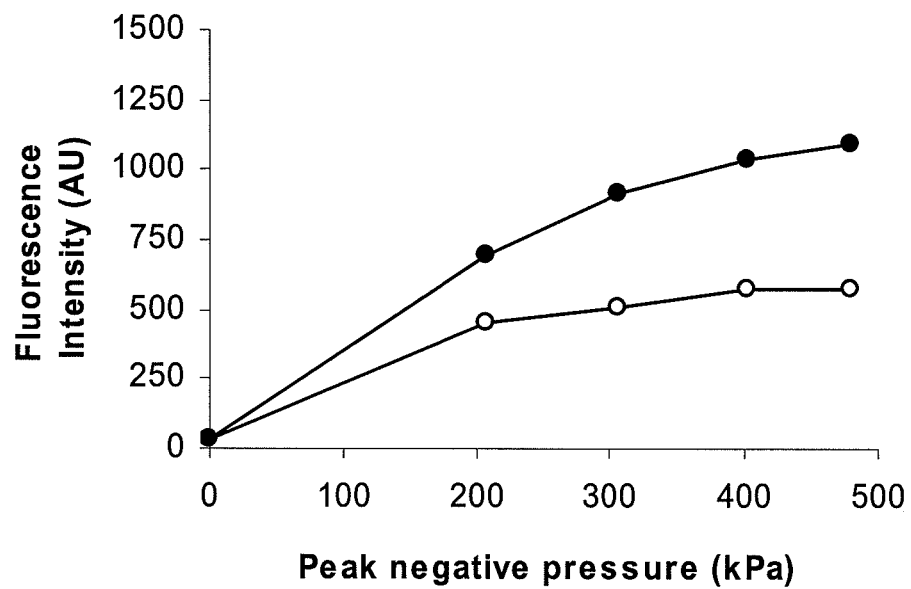
FIG. 4 shows the mean fluorescence intensities of GFP-positive cells measured upon ultrasound mediated gene delivery by using compositions containing microcapsules filled with different gases.

The measured mean fluorescence intensities (determined as above described) are reported in FIG. 4 (example 3: white circles; example 4: black circles). From FIG. 4, it can be observed that the cells insonated in the presence of microcapsules filled with a perfluorinated gas show a much higher mean fluorescence intensity (almost double) with respect to microcapsules filled with air.

Example 15

Gene Delivery by Insonation

Effect of Adjuvants

Four aliquots of the formulations prepared according to example 3, are added to respective sample tubes containing a cell suspension and plasmid as described above. Polyethylene glycol 4000 ($PEG_{4000}$) (Fluka, Buchs, Switzerland), Pluronic F68 or Pluronic F127 (both supplied by Sigma, Buchs, Switzerland) are separately added to the cell suspension at 0.05% w/v before ultrasound exposure. Then microcapsules are added in the suspension and cells are insonated with the transducer T2 at the acoustic pressures of 571 KPa with the ultrasound delivery system as described above. Condition with microcapsules, without adjuvant and exposed to ultrasound is used as control.

It is found that adjuvants like $PEG_{4000}$ and Pluronic F68/127 improve the percentage of GFP-positive cells by at least 20%, as compared to control.

Example 16

In Vivo Gene Delivery by Insonation with Polymeric Microcapsules

Animal Preparation and Ultrasound Exposure System $5 \times 10^6$ MAT B III cells (rat mammary adenocarcinoma, #CRL-1666 from ATCC) are injected subcutaneously (100 µL) into the fat mammary pad of female Fischer 344 rats, six days before treatment.

A 1 MHz focused transducer (T3) is mounted onto a water-filled plexiglass tube of 100 mm length, allowing insonation to be effected at the desired near field distance (100 mm). Details of transducer T3 are as follows:

| Manufacturer | Operating Frequency [MHz] | Type | Aperture [mm] | Near field distance [mm] |
|---|---|---|---|---|
| T3 Vermon | 1 | Focused | 40 | 100 |

The ultrasound delivery system further comprises a power RF amplifier ENI A150 (ENI, Rochester, N.Y.) and an arbitrary waves generator Tabor 8024 (Tabor Electronics Ltd, Hanan, Israel)

Tumors are insonated at a peak negative pressure of 1 MPa, with a duty cycle (DC) of 3% and a pulse repetition frequency (PRF) of 100 Hz, for 60 seconds. The central axis of the ultrasound propagation is focused on the tumor, and does not interfere with other parts of the rat. In each experiment, a diagnostic system (linear probe operating at a transmitted frequency of 4 MHz, L7-4 probe, ATL, HDI-5000, version 10.5, Philips ultrasound, Bothell, Wash., USA) is used to image the tumor (B-mode) and to assess both intratumoral microcapsules distribution after injection and microcapsules destruction following insonation. All echographic data are recorded on video tape.

In Vivo DNA Delivery

Rats are anaesthetized by injection of ketamine/xilazine (1 mL/kg). After depilation, a mixture containing microcapsules formulations prepared according to example 3 (3 µL or 10 µL, equivalent to 2.6 and 8.6×10$^6$ microcapsules) and 20 µL of a 1 mg/mL solution of plasmid DNA encoding for the luciferase protein (pGL3 Luciferase Reporter vector, Promega—Catalys AG, Wallisellen, Switzerland) is intratumorally injected using a 27G needle (the needle is left in place for 30 seconds after injection and then withdrawn slowly). Then, the tumor is insonated using the customized probe detailed above. Insonation is conducted via an ultrasound-conducting gel to ensure good ultrasound transmission.

In control experiments intratumoral injection of DNA in phosphate-buffered saline (PBS) is performed without microcapsules, followed by insonation under similar ultrasound conditions.

Tumor Analysis

For quantitative analysis of transfection, tumors are excised 48 hours after insonation, and homogenized in 5 mL of Cell Culture Lysis Reagent (Promega—Catalys AG, Wallisellen, Switzerland) at 18000 rpm for 20 seconds, using a POLYTRON® homogeniser. The homogenates are then centrifuged at 1000 g for 10 minutes and the supernatant is analyzed with a luminometer (Victor$^2$, Perkin Elmer, Courtaboeuf, France) using the luciferase Promega kit (Luciferase Assay Reagent, Promega—Catalys AG, Wallisellen, Switzerland). Luciferase activity is calibrated to the light unit per picogram (pg) of a standard solution of luciferase (Quanti-Lum® Recombinant Luciferase, Promega—Catalys AG, Wallisellen, Switzerland). The final result is expressed as pg of luciferase per g of tumor.

As shown in table 1 below transfection efficiency is higher in tumors injected with microcapsules and insonated as compared to control tumors. Moreover gene delivery efficiency increases with the dose of injected microcapsules.

TABLE 1

In vivo gene delivery in rat tumors mediated by ultrasound

|  | pg of luciferase/g of tumor |
| --- | --- |
| Control tumors (n = 3): without microcapsules + DNA + US | 0.7 |
| Treated tumors (n = 4): 2.6 × 10$^6$ microcapsules + DNA + US | 2.4 |
| Treated tumors (n = 6): 8.6 × 10$^6$ microcapsules + DNA + US | 6.3 |

Example 17

In Vivo Drug Delivery by Insonation with Microcapsules

Animal Preparation

R3230 mammary adenocarcinoma cells, harvested from live carrier and homogenized, are implanted in female Fisher 344 rats. R3230 cells in suspension (0.2 mL, about 1×10$^7$ tumor cells) are injected subcutaneously in a mammary pad on each side of the abdomen in each animal (10-12 weeks old). Tumors are grown for about 20 days until the desired size is achieved. Solid 10-15 mm-diameter non-necrotic tumors are used for insonation experiments.

In Vivo Doxorubicin Delivery by Ultrasound Exposure

A total of 10 rats with 2 tumors each are used for the experiments. One tumor of each pair is used as an internal control, thus is not exposed to ultrasound. Rats are anaesthetized by injection of ketamine/xilazine (1 ml/kg). Then liposomal doxorubicin (Caelyx®, Schering-Plough) is injected slowly into the jugular vein (via a chronic catheter) at a dose of 8 mg/kg of body weight with a 27-gauge needle (1 mg of doxorubicin in 500 µL). After 10 minutes, microcapsules formulations prepared according to example 3 are infused in the jugular vein at a flow rate of 0.1 mL/min (5×10$^8$ microcapsules/mL). Then 30 seconds later, a 1 MHz transducer (T4) mounted in a water-filled plexiglass tube of 50 mm length, allowing insonation of tumors at the near field distance, is used to insonate one of the tumor. Details of transducer T4 are as follows:

| Manufacturer | | Operating Frequency [MHz] | Type | Aperture [mm] | Near field distance [mm] |
| --- | --- | --- | --- | --- | --- |
| T4 | Imasonic | 1 | Unfocussed air-backed | 12.7 | 50 |

The ultrasound delivery system further comprises a power RF amplifier ENI A150 (ENI, Rochester, N.Y.), and an arbitrary waves generator Tabor 8024 (Tabor Electronics Ltd, Hanan, Israel). One of the tumor is randomly selected to be insonated under controlled conditions (1.5 MPa, 40% duty cycle, pulse repetition frequency of 100 Hz, 12 times 5 seconds exposure duration, pulsing interval of 30 seconds to allow the maximal refilling of microcapsules in the tumor vasculature), the second tumor serves as a control. The total volume of injected microcapsules is about 1 ml.

Quantification of Intratumoral Doxorubicin

The fluorescent properties of doxorubicin (DOX) are used to quantify the intratumoral amount of doxorubicin. R3230 tumors are harvested 24 hours after treatment, weighted, and homogenised with an Ultra-Turrax in Tris buffer pH 7 containing internal standard Daunorubicin (DNR) (Fluka, Buchs, Switzerland). Then samples are centrifuged at 8800 g for 10 minutes, and 200 µL of the supernatant is mixed with 125 µL of Triton X-100 solution (3% v/v) and 675 µL of 5 mM ammonium formate buffer pH 4.5. The suspension is briefly centrifuged and subjected to solid phase extraction. The processed samples are then analyzed by High Performance Liquid Chromatography (HPLC) using a reversed phase column. The eluted compounds of interest, namely DOX and DNR are monitored with a fluorescence detector. The excitation and emission wavelengths are set at 475 and 550 nm, respectively. Samples are always handled in absence of light and in polypropylene tubes.

Tumors exposed to ultrasound in presence of microcapsules display a higher concentration of doxorubicin as compared to control tumors non insonated, thus indicating an improvement of drug delivery.

The invention claimed is:

1. A method for delivering a bioactive agent into a cell which comprises:
    administering a composition comprising a bioactive agent and a plurality of gas filled microcapsules having a polymeric and/or lipid shell to a body part comprising said cell in a patient in need thereof, said microcapsules having a resistance to a mechanical index of at least 0.15 and not higher than 10, and said bioactive agent being substantially unbound to and located outside of said shell; and applying an ultrasound wave to said body part, said wave having a frequency of from about 20 kHz to less than about 50 MHz and an acoustic pressure that results in a mechanical index that is capable of destroying a portion of said microcapsules, to effectively deliver said bioactive agent to said cell.

2. The method of claim 1 wherein the shell of said microcapsules comprises a biodegradable physiologically compatible polymer and/or a biodegradable water-insoluble lipid.

3. The method of claim 1 wherein the gas contained in the microcapsules comprises a perfluorinated gas.

4. The method of claim 1 wherein said bioactive agent is a drug or a genetic material.

5. The method of claim 1 wherein said bioactive agent is associated with a carrier.

6. The method of claim 5 wherein said carrier further comprises a targeting ligand.

7. The method of claim 1, wherein-said microcapsules have a resistance to a mechanical index of at least 0.18 and not higher than 10.

8. The method of claim 7, wherein-said microcapsules have a resistance to a mechanical index of at least 0.20 and not higher than 10.

9. The method of claim 1, wherein said acoustic pressure is from 200 kPa to 10 MPa and said frequency is 1.15 MHz.

10. The method of claim 1, wherein said acoustic pressure is from 300 kPa to 10 MPa and said frequency is 2.25 MHz.

11. The method of claim 1, wherein said frequency is from about 300 kHz to about 3 MHz.

12. The method of claim wherein said frequency is from about 500 kHz to about 1.5 MHz.

13. The method of claim 1, wherein said frequency is about 1 MHz.

14. The method of claim 1, wherein said wave has a spatial-peak time-average intensity of from about 0.5 mW/cm$^2$ to about 10 W/cm$^2$.

15. The method of claim 1, wherein said wave has a spatial-peak time-average intensity of from about 1 mW/cm$^2$ to about 3 W/cm$^2$.

16. The method of claim 14, wherein the total energy deposition is below the cytotoxic threshold of said cell.

* * * * *